United States Patent
Ries

(10) Patent No.: US 10,342,677 B2
(45) Date of Patent: Jul. 9, 2019

(54) INSTRUMENT SET AND METHOD FOR INSERTING A CAGE INTO THE INTERVERTEBRAL DISK SPACE BETWEEN TWO VERTEBRAL BODIES

(71) Applicant: JOIMAX GMBH, Karlsruhe (DE)

(72) Inventor: Wolfgang Ries, Linkenheim-Hochstetten (DE)

(73) Assignee: JOIMAX GMBH, Karlsruhe (DE)

( * ) Notice: Subject to any disclaimer, the term of this patent is extended or adjusted under 35 U.S.C. 154(b) by 203 days.

(21) Appl. No.: 14/778,816

(22) PCT Filed: Mar. 21, 2014

(86) PCT No.: PCT/EP2014/000779
§ 371 (c)(1),
(2) Date: Sep. 21, 2015

(87) PCT Pub. No.: WO2014/146797
PCT Pub. Date: Sep. 25, 2014

(65) Prior Publication Data
US 2016/0045334 A1 Feb. 18, 2016

(30) Foreign Application Priority Data

Mar. 22, 2013 (DE) .................. 10 2013 004 964
Aug. 14, 2013 (DE) .................. 20 2013 007 361 U

(51) Int. Cl.
A61F 2/46 (2006.01)
A61F 2/44 (2006.01)
A61F 2/30 (2006.01)

(52) U.S. Cl.
CPC ............ *A61F 2/4611* (2013.01); *A61F 2/447* (2013.01); *A61F 2002/30011* (2013.01); *A61F 2002/30013* (2013.01); *A61F 2002/30172* (2013.01); *A61F 2002/30289* (2013.01); *A61F 2002/30428* (2013.01); *A61F 2002/30538* (2013.01);
(Continued)

(58) Field of Classification Search
CPC .... A61F 2/44; A61F 2/447; A61F 2/46; A61F 2/4611
See application file for complete search history.

(56) References Cited

U.S. PATENT DOCUMENTS 5,257,975 A * 11/1993 Foshee ................... A61B 17/34
604/105
8,979,861 B2 * 3/2015 Cloutier ............. A61B 17/7074
606/79

(Continued)

FOREIGN PATENT DOCUMENTS

CN 101106958 A 1/2008
CN 102429718 A 5/2012
(Continued)

*Primary Examiner* — Christopher Beccia
(74) *Attorney, Agent, or Firm* — McGlew and Tuttle, P.C.

(57) ABSTRACT

For inserting a cage in the intervertebral disk space between two vertebrae, an instrument set includes a guide wire with a plurality of dilators that can be pushed over the guide wire and one over another, with a working sleeve and with a cage, in which the working sleeve is designed in its distal area such that it makes possible the fixation of its distal area in the direction of its extension with angular mobility or variable angular orientability of its proximal end.

24 Claims, 21 Drawing Sheets

(52) U.S. Cl.
CPC ............... *A61F 2002/30604* (2013.01); *A61F 2002/30616* (2013.01); *A61F 2002/30795* (2013.01); *A61F 2002/30909* (2013.01); *A61F 2002/4475* (2013.01); *A61F 2002/4495* (2013.01); *A61F 2002/4627* (2013.01); *A61F 2310/00023* (2013.01)

(56) References Cited

U.S. PATENT DOCUMENTS

| | | |
|---|---|---|
| 2001/0016741 A1 | 8/2001 | Burkus et al. |
| 2004/0106997 A1 | 6/2004 | Lieberson |
| 2005/0251257 A1* | 11/2005 | Mitchell ............... A61F 2/4465 623/17.11 |
| 2006/0064100 A1 | 3/2006 | Bertagnoli et al. |
| 2006/0074488 A1 | 4/2006 | Abdou |
| 2007/0021835 A1 | 1/2007 | Edidin |
| 2007/0106319 A1 | 5/2007 | Au et al. |
| 2007/0162138 A1 | 7/2007 | Heinz |
| 2007/0213826 A1 | 9/2007 | Smith et al. |
| 2008/0097398 A1* | 4/2008 | Mitelberg ......... A61M 25/0043 604/525 |
| 2009/0138043 A1 | 5/2009 | Kohm |
| 2010/0318028 A1 | 12/2010 | Tsuang et al. |
| 2011/0319995 A1* | 12/2011 | Voellmicke ........... A61F 2/4455 623/17.11 |
| 2012/0059480 A1 | 3/2012 | Schell et al. |
| 2012/0078315 A1 | 3/2012 | Sweeney |
| 2012/0197263 A1 | 8/2012 | Copf et al. |
| 2012/0232552 A1* | 9/2012 | Morgenstern Lopez .................... A61B 18/1487 606/45 |
| 2013/0006362 A1* | 1/2013 | Biedermann ......... A61F 2/4465 623/17.16 |
| 2013/0190769 A1 | 7/2013 | Morgenstern Lopez et al. |

FOREIGN PATENT DOCUMENTS

| | | |
|---|---|---|
| CN | 102824233 A | 12/2012 |
| DE | 10 2008 045174 A1 | 3/2010 |
| DE | 20 2010 011 773 U1 | 11/2010 |
| EP | 0 077 159 A1 | 4/1983 |
| EP | 1 634 549 A2 | 3/2006 |
| EP | 2 422 753 A1 | 2/2012 |
| WO | 01/60263 A1 | 8/2001 |
| WO | 2011/094748 A1 | 8/2011 |
| WO | 2012122294 A1 | 9/2012 |

* cited by examiner

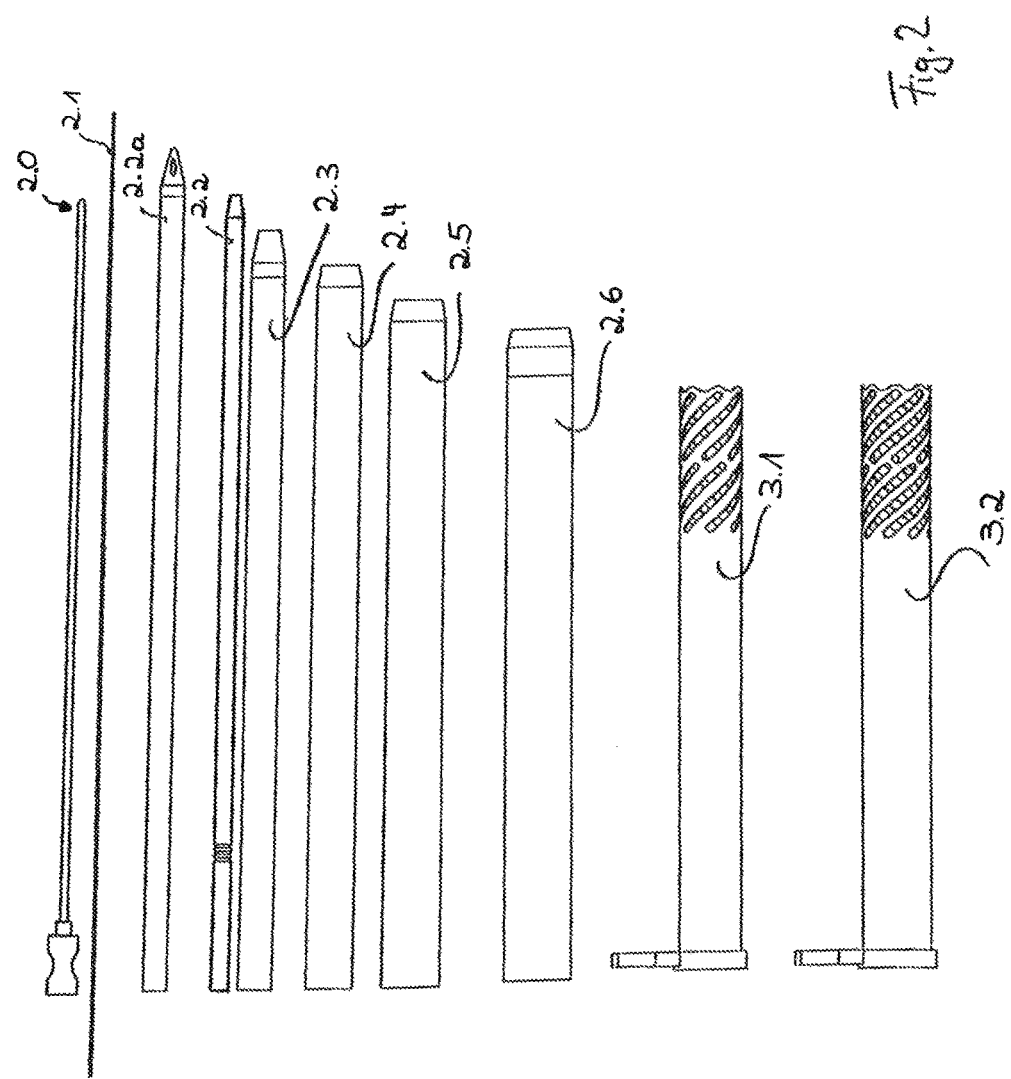

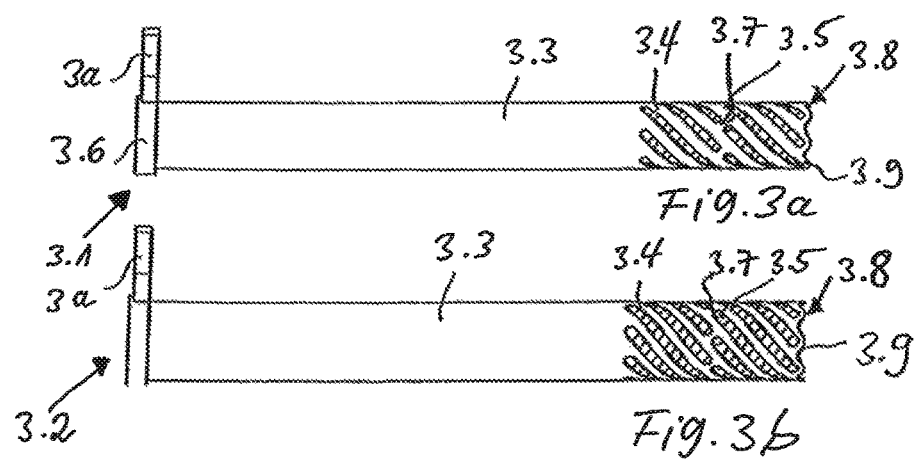

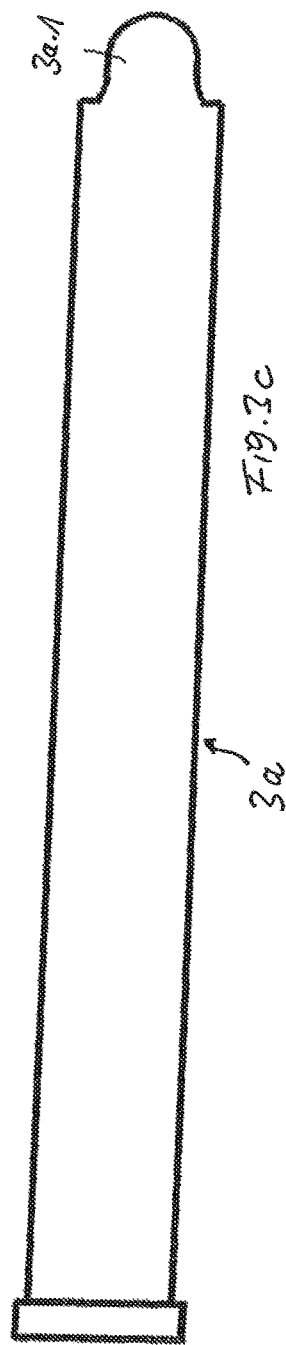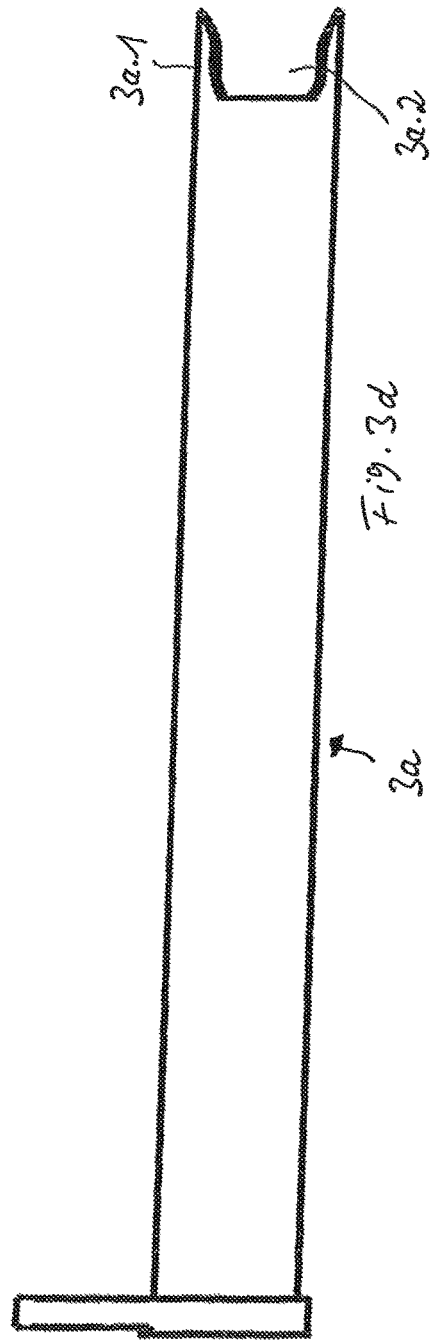

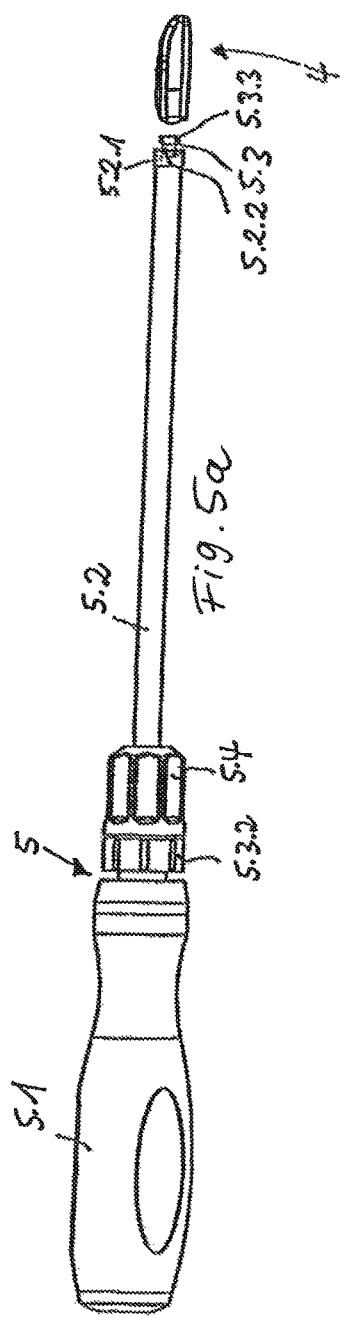
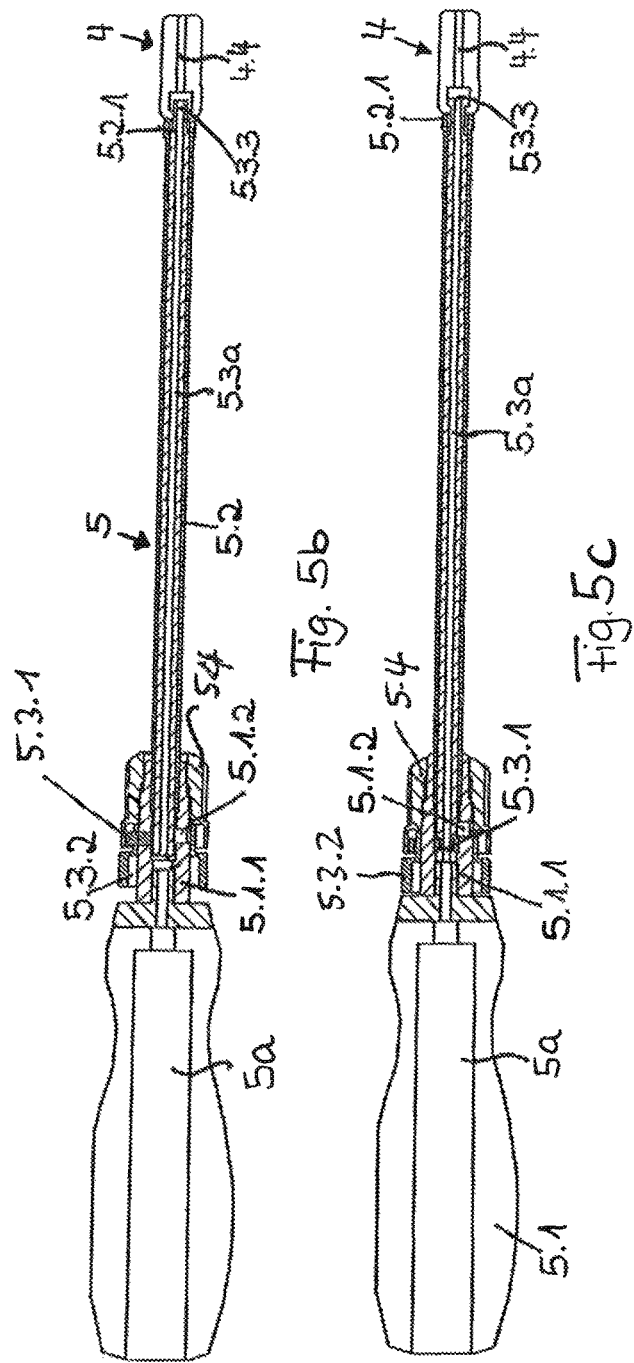

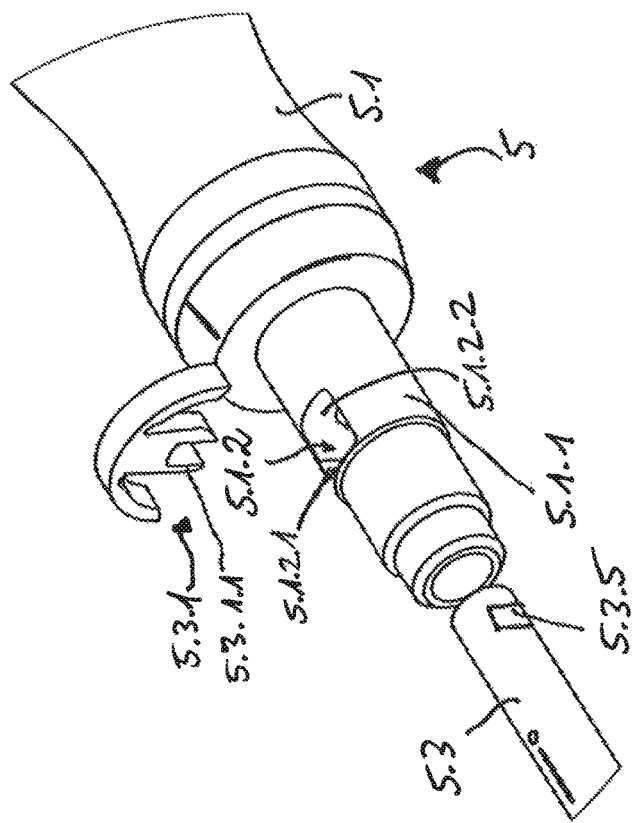

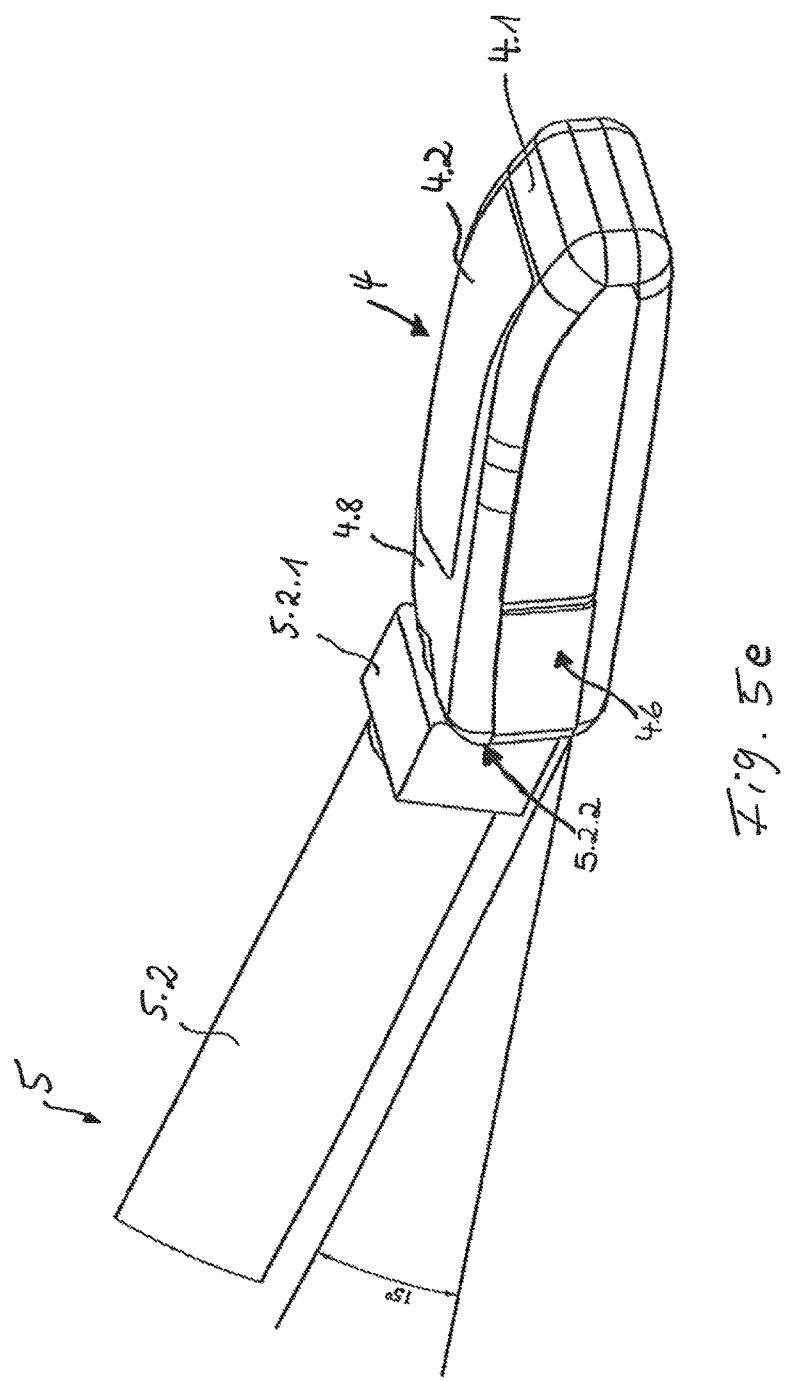

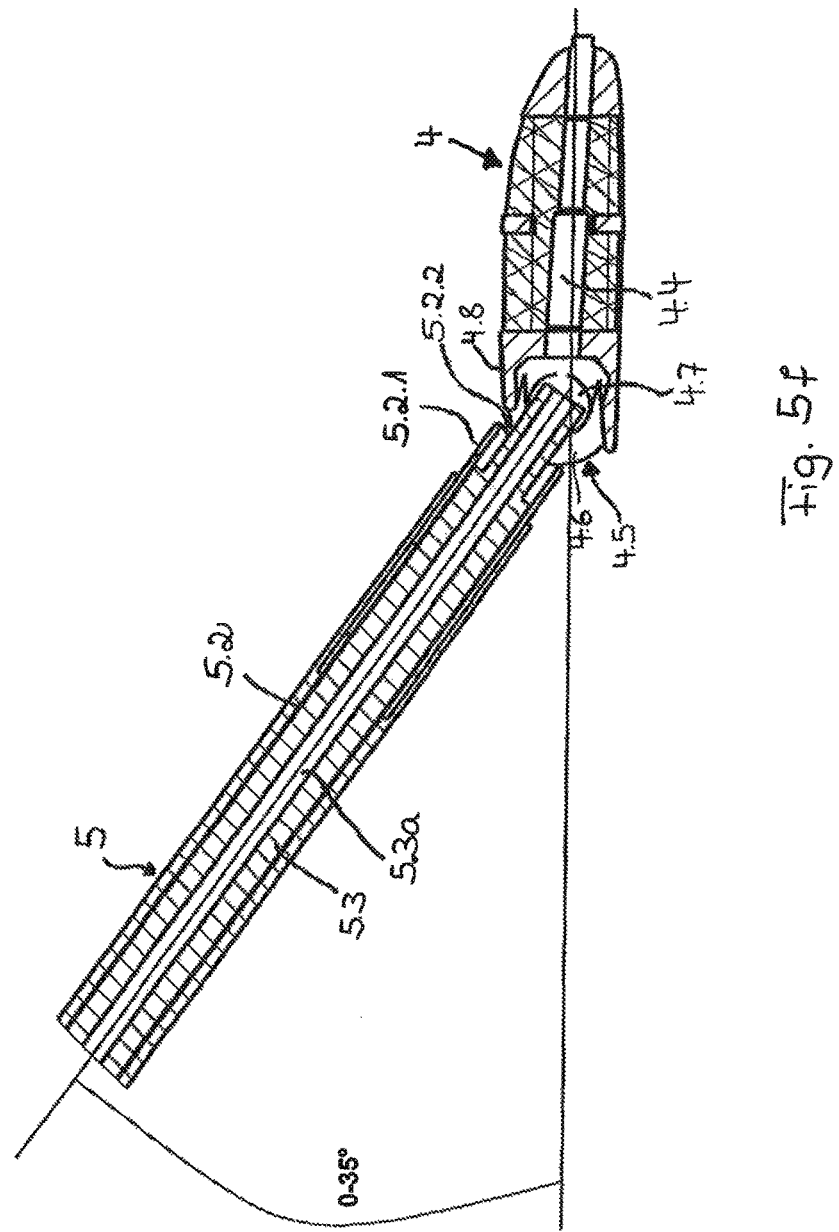

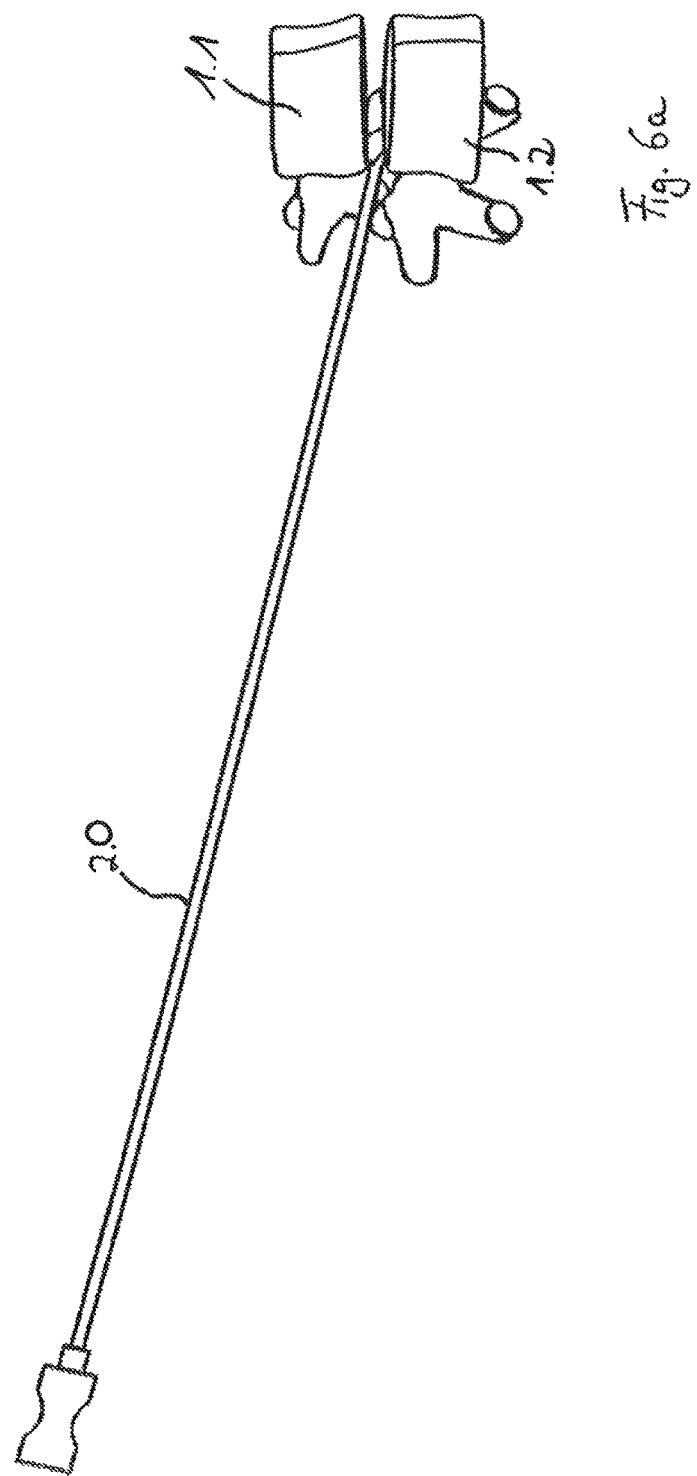

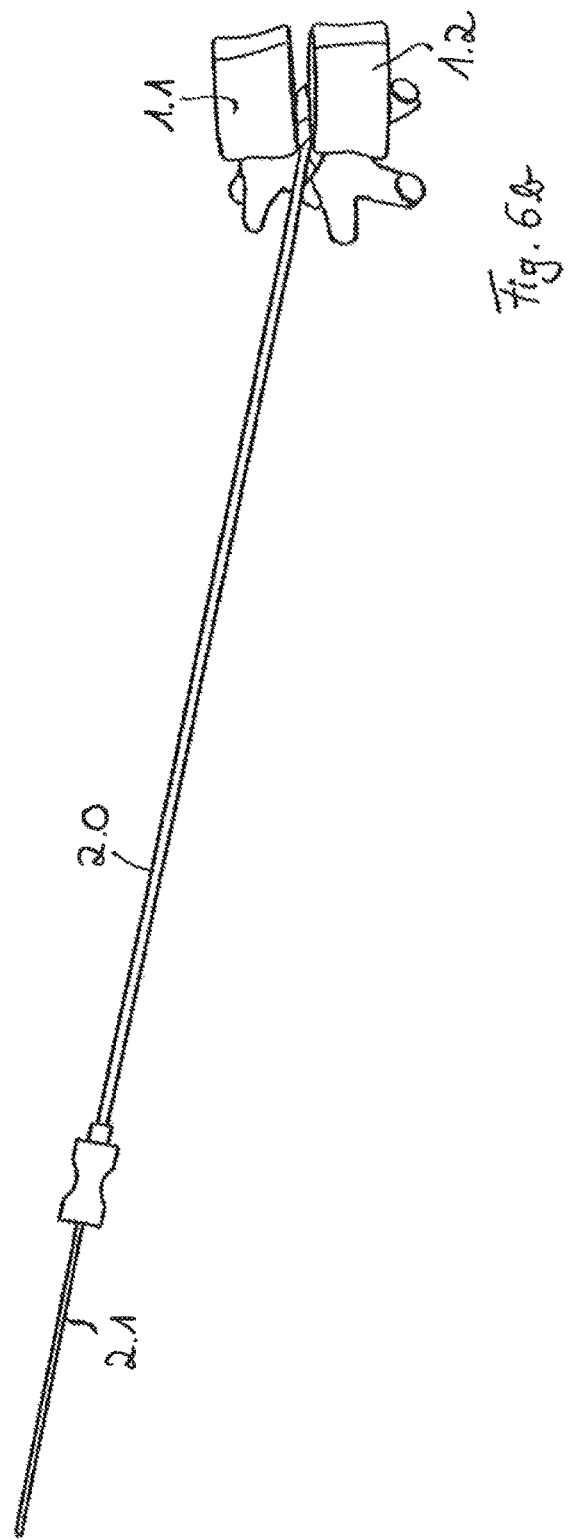

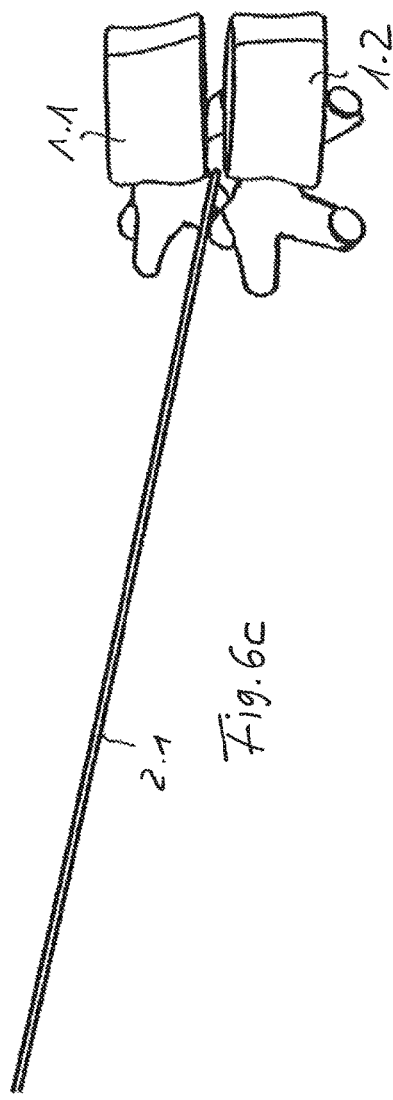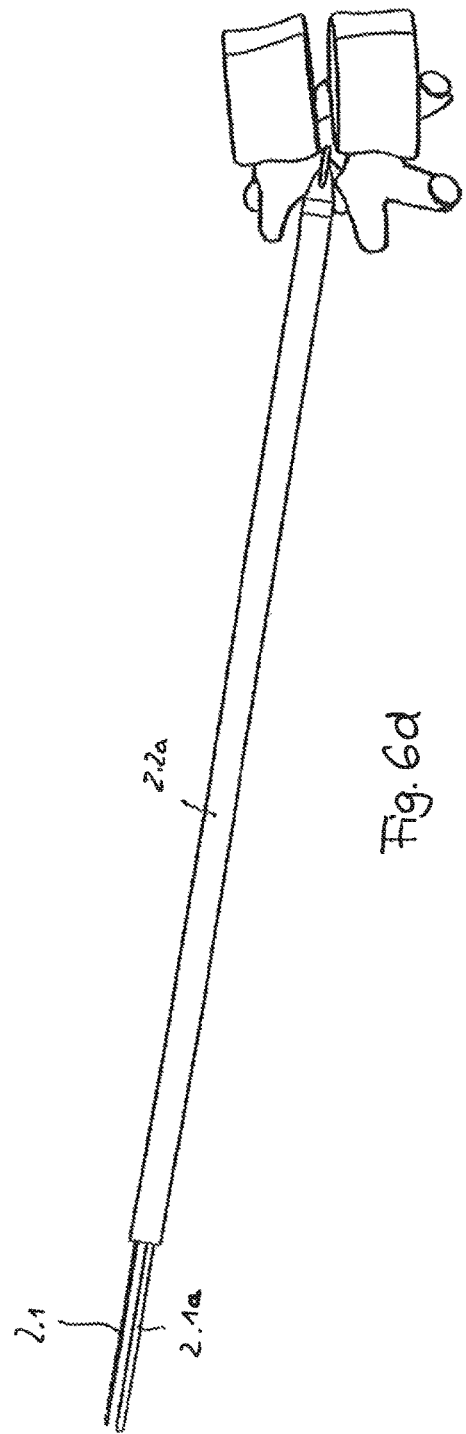

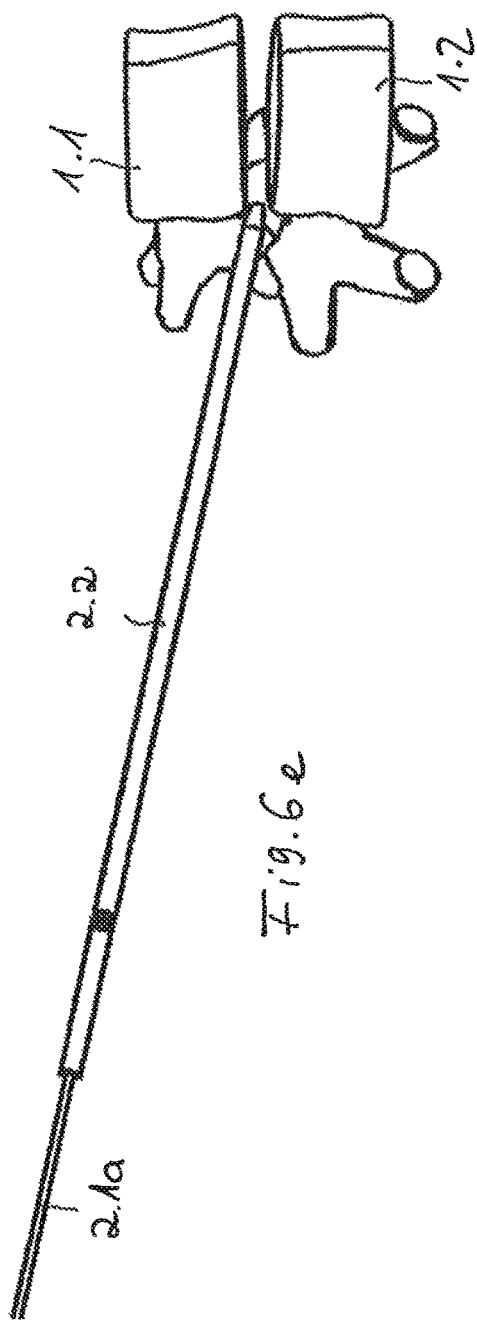

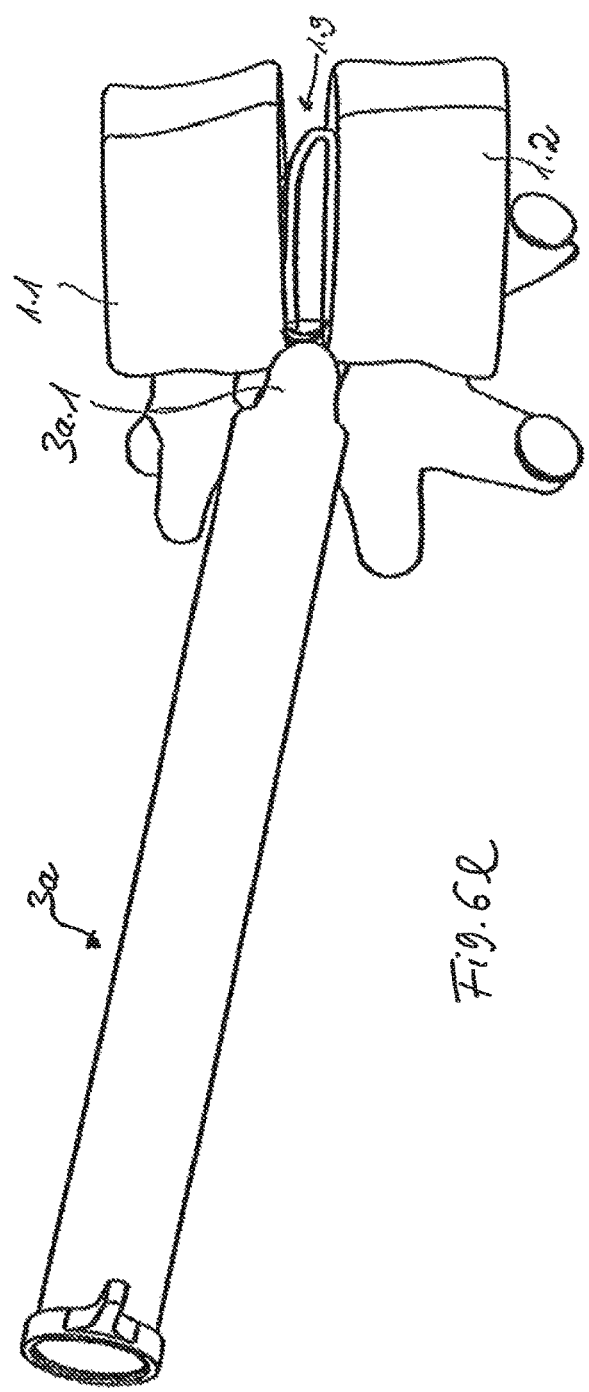

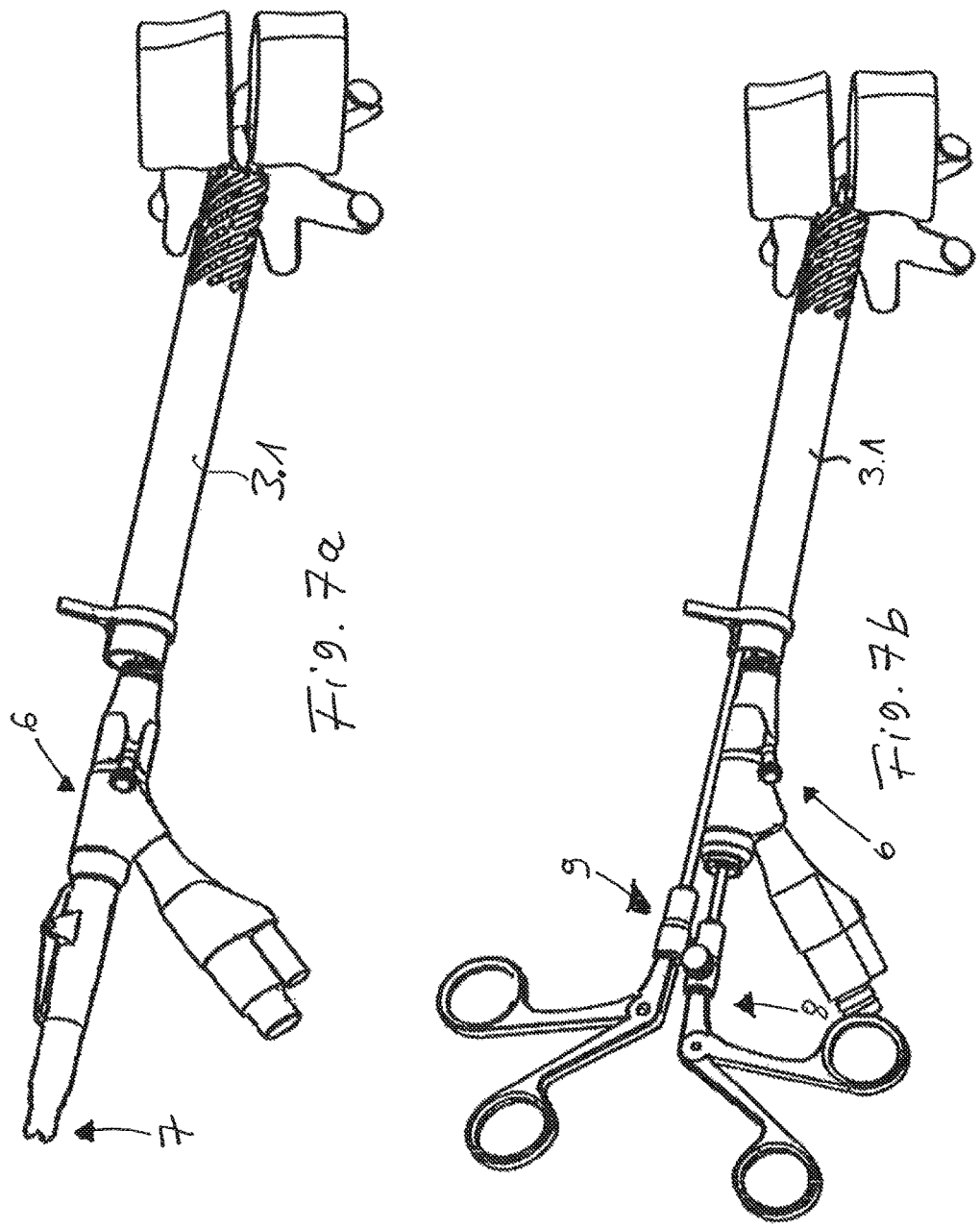

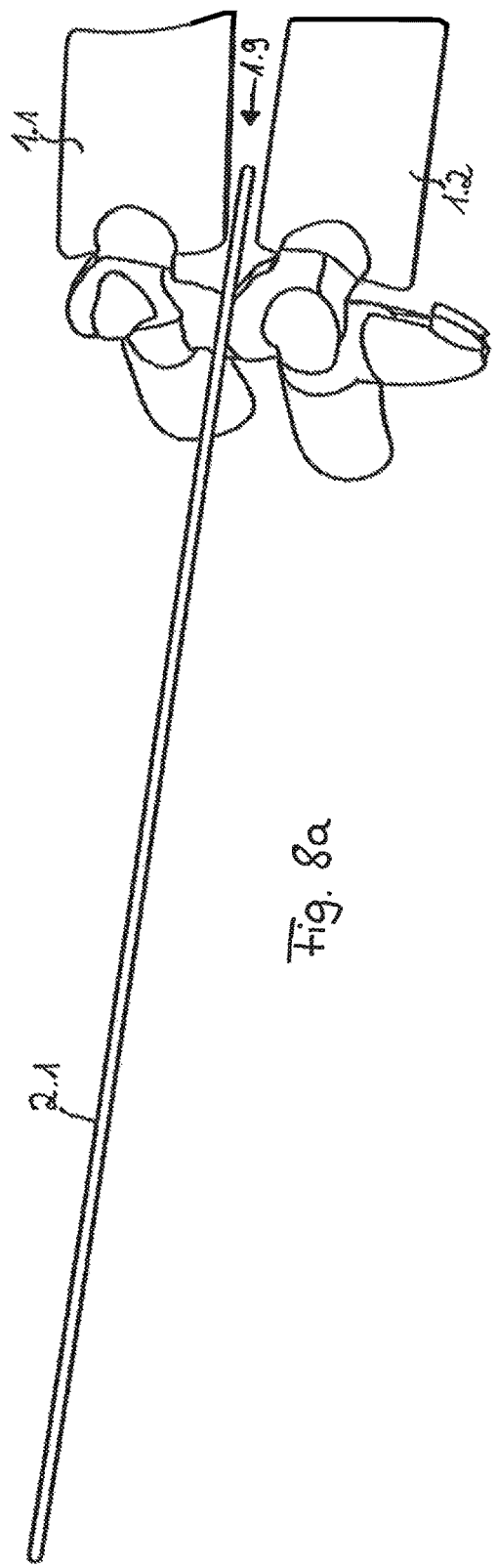

INSTRUMENT SET AND METHOD FOR INSERTING A CAGE INTO THE INTERVERTEBRAL DISK SPACE BETWEEN TWO VERTEBRAL BODIES

CROSS REFERENCE TO RELATED APPLICATIONS

This application is a United States National Phase application of International Application PCT/EP2014/000779 filed Mar. 21, 2014 and claims the benefit of priority under 35 U.S.C. § 119 of German patent applications DE 10 2013 004 964.4 filed Mar. 22, 2013 and DE 20 2013 007 361.6 filed Aug. 14, 2013, the entire contents of which are incorporated herein by reference.

FIELD OF THE INVENTION

The present invention relates to an instrument set for inserting a cage into the intervertebral disk space between two vertebral bodies, with a guide rod, with a plurality of dilators, which can be pushed over the guide rod and over one another, with a working sleeve and with a cage, and to a method for inserting a cage into the intervertebral disk space between two vertebral bodies, wherein at first a hollow needle and then, through this, a guide wire are inserted into the intervertebral disk space, the hollow needle is removed, after which dilators with consecutively larger diameters are pushed over the guide wire one after another and one over another, and, further, a working sleeve is inserted via the last dilator up to the vertebral bodies and the guide wire as well as the dilators are removed from the working sleeve.

BACKGROUND OF THE INVENTION

Reinforcement of the spine between the two vertebral bodies affected by the lesion is performed in a number of spinal lesions, especially lesions to intervertebral disks, such as spondylolisthesis and instability following disk herniation and stenosis. An interbody cage is inserted for this between the vertebral bodies into the scooped-out intervertebral disk space, and the vertebral bodies fuse with the cage. This is called, e.g., lumbar interbody fusion or LIF. There are similar methods for the thoracic spine and the cervical spine. A skin incision is usually made for this in order to be able to reach the intervertebral disk space under visible conditions, and this is accompanied by muscle destruction. In addition, percutaneous screws embedded by minimally invasive spinal surgery with screw-rod systems may contribute to the overall stabilization.

The prior-art techniques for gaining access for inserting cages into the intervertebral disk space between vertebral bodies are subject to drawbacks and risks.

SUMMARY OF THE INVENTION

A basic object of the present invention is to provide an instrument set and a method for inserting a cage into the intervertebral disk space, with which the cage can be inserted into the intervertebral disk space in a simple and uncomplicated manner and with the lowest possible risk of damage to the patient.

This object is accomplished according to the present invention with an instrument set of the type described in the introduction, which is characterized in that the working sleeve is designed in its distal area such that it makes it possible to fix its distal area in the direction of its extension while its proximal end has angular mobility or can be oriented at variable angles. All parts of the instrument set according to the present invention, especially those penetrating into the body, consist, in principle, of metal, especially stainless steel.

Thus, the present invention makes provisions for the working sleeve of the instrument set, which is in place after dilatation of the access path to the working site, the intervertebral disk space, to be able to be anchored there and to find an abutment at the two vertebrae defining the intervertebral disk space above and below in such a way as to be axially fixed, on the one hand, and, on the other hand, for its orientation, especially that of its proximal end, relative to the intervertebral disk space and to the vertebral defining same, or to the spine, especially relative to the direction of extension of the spine, to be variable, and thus for the working sleeve to be mobile to a certain extent.

Provisions are made in preferred embodiments for the working sleeve to have a flexible design in its distal area and/or for the working sleeve to be designed as a wedge sleeve. Provisions may preferably be made for this for the working sleeve to have in its distal end area two mutually diagonally opposite projections extending with parallel axes, leaving recesses free, the projections being provided with a rounding each especially at their distal free end.

The angular adjustability or mobility of the sleeve is achieved in the first embodiment by the distal end area of the sleeve being flexible. In the second embodiment, this is achieved by the distal ends of the sleeve having said contours, which make possible an axial fixation at the vertebrae defining the intervertebral disk space in different angular orientations. This embodiment offers, moreover, the further advantage that the intervertebral disk space can be kept open even after the intervertebral disk had been scooped out by the wedge-shaped projections, which protrude between the adjacent vertebrae in the intervertebral disk space; the vertebrae can thus be kept at a distance in this way.

Provisions are, furthermore, made in preferred embodiments of the instrument set for the cage and an inserting instrument for inserting the cage to have locking elements each interacting with one another, which form a common locking, wherein especially the locking of the inserting instrument and the cage permit an angular mobility of both parts.

Provisions may be made in a variant for the working sleeve to be provided with slots with ribs arranged between them in its distal jacket area; the slots impart an elasticity and flexibility on the distal end area of the working sleeve, while the rigidity is still sufficient. The slots extend especially around the jacket of the working sleeve along helical lines, i.e., helically or in a helical pattern. Moreover, a preferred embodiment of the instrument set according to the present invention is characterized in that at least two slots are arranged flush one after another on a helical line separated by a web, and, furthermore, the widths of slots, ribs and webs is between 0.5 mm and 2 mm.

The slots extend helically especially from their proximal end to their distal end from left to right or clockwise when viewing from the proximal end of the sleeve. Easy insertion of the working sleeve during counterclockwise rotation is made possible hereby. The sleeve is finally fixed by clockwise rotation, as a result of which "docking" or fixation by surrounding muscle fibers is brought about. Muscle fibers, but also nerves, which may enter the interior of the sleeve, as well as hemorrhages can be detected endoscopically during the operation.

Provisions are made in another embodiment for the cage to have an opening of a greater height than width as a locking element on an end face, wherein the opening is provided in the direction of its opening with an undercut, wherein the inserting element has a rod with a radially extending plate with a width that is greater than the height, which said plate is designed as a locking element at the distal end and is pivotable by means of a grip about the axis of the rod.

The flexibility or bendability of the working sleeve in the distal area may, in principle, also be achieved in another manner, for example, by a sequence of two or three circumferential slots provided each in the axial direction with remaining ribs and webs. The helical or spiral embodiment offers the advantage that the working sleeve can thus be inserted more easily by the screwing motion, for which a radial lever is preferably provided proximally.

Provisions are made in variants of the instrument set for the inserting instrument to have a tube with a proximal gripping sleeve, through which tube the rod extends, so that the plate is pivotable relative to the tube, preferably by up to a relative angle of 55°, and for an abutment to be formed on the tube with two convex front edges extending in parallel to one another.

Provisions are made in another preferred embodiment of the set according to the present invention for the inserting instrument and the cage to have a through passage each. As a result, the inserting instrument with the cage connected to it can be pushed into the intervertebral space or the intervertebral disk space via a guide wire. Furthermore, the inserting instrument can thus be removed again via the guide wire after separation from the cage placed in the intervertebral disk space.

The cage is preferably provided with grid-like or lattice-like areas, especially with the structure of a diamond lattice cell. Lattice-like areas on the outer side of the cage have opening diameters at each opening on the order of magnitude of 500 μm to 700 μm and/or lattice-like areas in the interior of the cage have openings or perforations with diameters of 1,500 μm to 3,200 μm or a uniform opening diameter of 500 μm top 3,200 μm. The wall thickness of the material is preferably on the order of magnitude of 600 μm, especially 800 μm.

Moreover, the object according to the present invention is accomplished by a method of the type described in the introduction, which is characterized in that a working sleeve having a flexible design in its distal jacket area is pushed in, that a cage with at least a partially porous structure is pushed into the intervertebral disk space through the working sleeve by means of an inserting instrument, with which the cage is locked, after removal of the intervertebral disk from the intervertebral disk space, after which the locking between the cage and the inserting instrument is released, and the working sleeve is then removed. Aside from the fact that the further drawbacks of the state of the art are avoided, no facet joint resection is, in particular, necessary in the subject of the present invention.

Provisions may be made here, in particular, for the instruments to be inserted transcutaneously from the back at an angle greater than 45° and less than 70°, preferably greater than 55° and less than 65° relative to the processus spinosus up to the vertebral body, and, moreover, the instruments are inserted from the back on the side of a transverse process facing away from the dorsal surface on the vertebral bodies.

Furthermore, provisions may be made for a working sleeve to be inserted in its distal jacket surface with slots and webs arranged between these via the dilators, wherein especially a working sleeve with helically extending slots is inserted into a helical motion via the dilators, and/or that a porous cage is inserted through the working sleeve into the intervertebral disk space, wherein especially a cage with a coarser porosity in the interior and finer porosity on the outer area is inserted.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 2 is a side view of an access instrument or access instruments of the device according to the present invention;

FIG. 3a is a side view of a working sleeve with one diameter;

FIG. 3b is a side view of another working sleeve with a diameter that is different from the working sleeve of FIG. 3a;

FIG. 3c is a side view of an alternative working sleeve in the form of a wedge sleeve;

FIG. 3d is a top view of a wedge sleeve from FIG. 3c at right angles to the axis;

FIG. 4b is a perspective view of the O-cage according to FIG. 4a;

FIG. 5a is a view of an inserting instrument and cage (O-cage) in front of the device;

FIG. 5b is a horizontal longitudinal sectional view through an inserting instrument in the insertion position;

FIG. 5c is a horizontal longitudinal sectional view of an inserting instrument in the locked position in relation to the cage;

FIG. 5d is an enlarged detail view of proximal parts of the inserting instrument;

FIG. 5e is a view of the distal area of the inserting element with coupled cage to illustrate the angular mobility between the inserting instrument and the cage in the vertical direction with locking established;

FIG. 5f is a longitudinal sectional view corresponding to FIG. 5d of a modified embodiment;

FIG. 6a is a view of a hollow needle placed through the intervertebral foramen up to the intervertebral disk space;

FIG. 6b is a view of a hollow needle with a guide wire inserted into same;

FIG. 6c is a view of a guide wire after removal of the hollow needle;

FIG. 6d is a view of a double-cannulated guide rod inserted via the guide wire with additional guide wire of a larger diameter;

FIG. 6e is a view of a first dilator (guide sleeve) pushed over the guide rod;

FIG. 6*l* is a view of a working sleeve of a second embodiment, anchored on the vertebral bodies with its end face, in the form of a wedge sleeve after removal of the guide rod and the dilators;

FIG. 7*a* is a view of an endoscope inserted through the working sleeve with a rotatable mill inserted through this endoscope up to the vertebral bodies for removing vertebral body material to expand the intermediate space between the vertebral bodies;

FIG. 7*b* is a view of the working sleeve docked at the vertebral segment with the endoscope inserted as well as with tools passed through this, in the form of two different forceps for removing intervertebral disk tissue;

FIG. 8*a* is a view showing the course of insertion of a cage by means of an insertion tool via a guide wire into the intervertebral space;

DESCRIPTION OF THE PREFERRED EMBODIMENTS

The present invention pertains to the insertion of a cage into the intermediate space between two vertebral bodies of a vertebral segment, the intervertebral disk space, which is usually filled by intervertebral disk tissue, for replacing the intervertebral disk and for the permanent stabilization of the vertebral segment, usually called (lumbar) spinal fusion.

Figure 1A:
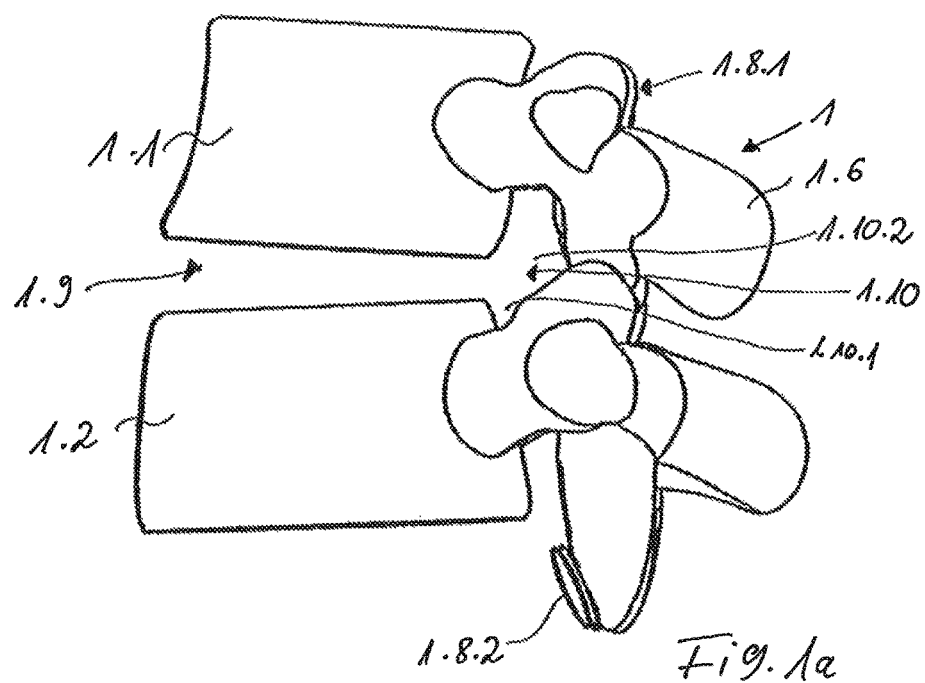
FIG. 1a is a side view of a vertebral segment comprising two vertebrae.

FIG. 1*a* shows in a side view a vertebral segment 1 of the spine comprising two vertebrae 1.1 and 1.2 and the intervertebral disk space 1.9 between these, in which the intervertebral disk (not shown) is located. It can be seen from the top view shown in FIG. 1*b* that a vertebra 1.1 comprises the vertebral body 1.2, the pedicles 1.4, which are formed from this laterally from the vertebral foramen 1.3 forming the vertebral canal, the adjacent vertebral arch 1.5 and—starting from this and connected by this—the central processus spinosus 1.6 as well as the transverse process 1.7 extending laterally at angles of about 60°. Vertebral joint facets 1.8.1 and 1.8.2 are formed on the pedicles 1.4, and a vertebral joint facet of one vertebra cooperates with that of the adjacent vertebra.

A space, the intervertebral disk space 1.9, in which the intervertebral disk (not shown) is located, remains between the two vertebral bodies 1.1 and 1.2. An intervertebral foramen or foramen intervertebrale 1.0 defined by an incisura vertebralis inferior 1.10.1 of the upper vertebra and an incisura vertebralis superior 1.10.2 of the lower vertebra is located between the pedicles 1.4 of two vertebrae located one above another.

As will be shown below, the present invention provides for access to the intervertebral disk space 1.9 between the vertebral bodies 1.1 and 1.2 via the intervertebral foramen 1.10 and laterally past same.

The instrument set 2 according to the present invention for inserting a cage into the intervertebral disk space 1.9 has, in the exemplary embodiment being shown, first the following instruments shown below in FIGS. 2 and 3*a*, 3*b*: A hollow needle 2.0, a guide wire 2.1, which is laterally flexible but is axially sufficiently rigid to be inserted especially through an incision in the skin of a patient at an angle between 45° and 70°, preferably between 55° and 65°, laterally past the intervertebral foramen 1.10 and into the intervertebral disk space 1.9 or directly into this (FIG. 6*a*).

A double-cannulated guide rod 2.2*a* with two lumens of approx. 1 mm and approx. 2 mm may be provided in order to optionally replace a thinner guide wire 2.1 with a thicker one.

Furthermore, a first dilator 2.2 is provided as a guide sleeve or guide rod, as well as additional dilators 2.2-2.6, a total of five dilators together with the guide sleeve in the exemplary embodiment being shown, and three, four or all five dilators are used depending on the size of the cage to be inserted. The internal diameter of the first dilator 2.2 corresponds to the external diameter of the guide wire 2.1, and the internal diameter of the second dilator 2.3 corresponds to the external diameter of the first dilator or guide sleeve 2.2. The internal diameters of the additional dilators 2.4 through 2.6 correspond to the external diameters of the dilators 2.3 through 2.5 having smaller cross sections. Even more dilators may be optionally provided. The dilators have external diameters of 8 mm to 25 mm, the dilators 2.5 and 2.6 having external diameters of 15 mm and 18 mm, respectively, in the exemplary embodiment being shown. The wall thickness is between 0.5 mm and 2 mm.

The dilators 2.3 through 2.6 are designed basically as cylinder jackets, but their wall is conically tapered from the outside to the inside at their distal ends. In addition, the length of the dilator with the respective larger diameter is smaller than the length of the dilator with the smaller diameter, as this is seen in FIG. 2. The dilators can be removed later in this manner from the inside one after another in a simple manner.

Furthermore, the instrument set 2 includes first a working sleeve 3.1 and 3.2, respectively, as this is shown in FIG. 3*a* and in FIG. 3*b*, respectively, the working sleeve 3.1 according to FIG. 3*a* having diameter ratios corresponding to the dilator 2.5 according to FIG. 2, so that it can be pushed over the dilator 2.4, while the internal diameter of the working sleeve 3.2 according to FIG. 3*b* corresponds to the external diameter of the dilator 2.5, so that the former can be pushed over the latter.

Three or four dilators, over which a working sleeve of a smaller diameter is then pushed, may possibly also be sufficient.

Figure 1B:
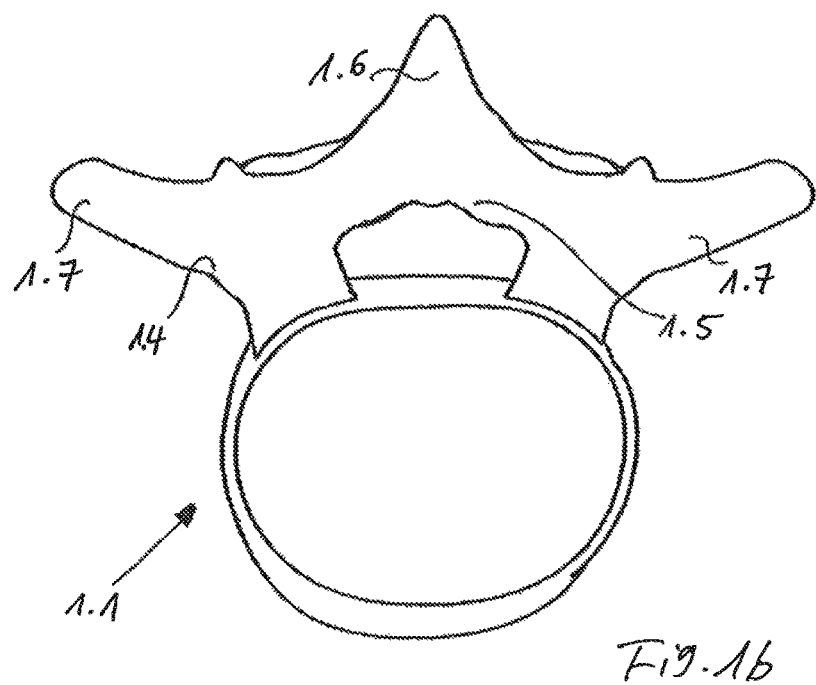
FIG. 1b is a top view of a vertebra from the top.

The distal end area of the working sleeves 3.1, 3.2 is made flexible over about one fourth to one third of the length of the working sleeve. This is achieved in the embodiment according to FIGS. 3*a* and 3*b* by slots 3.4 passing completely through the wall, between which ribs 3.5 remain, which are formed in the cylinder jacket 3.3 of the working sleeve 3.1 (and 3.2), wherein ribs 3.5 and slots 3.4 are led helically, clockwise when viewed from the proximal end face 3.6. The slots 3.4 do not extend continuously over the entire circumference, but only over about half of the circumference in the exemplary embodiments being shown and are interrupted by webs 3.7, which connect two adjacent ribs 3.5. Moreover, the distal end face 3.8 of the cylinder jacket wall of the working sleeves 3.1, 3.2 is also closed by webs 3.9, so that the slots do not end freely in the proximal end face 3.6. However, the distal end face of the jacket wall 3.3 of the working sleeves 3.1, 3.2 has a wave-shaped design with projections and depressions. Secure fixation of the working sleeve by the extended muscle tissue on the outer side of the two vertebral bodies 1.1, 1.2 is brought about hereby on the outer side of the two vertebral bodies 1.1, 1.2, into the intervertebral disk space 1.9 of which a cage shall be inserted (FiG. 1*a*, 1*b*). The instrument set may include, furthermore, an endoscope as well as working tools, such as mill, raspatories, drills, rasps and forceps, as they are known per se, but will also be described below. A radial lever 3*a*, with which the working sleeves can easily be inserted by screwing in via the dilators, is provided at the proximal end 3.6 of the working sleeves 3.1, 3.2. The working sleeves 3.1, 3.2 are used especially in case of O-cages (see below).

An alternative second embodiment of a working sleeve 3*a* in the form of a wedge sleeve is shown in FIGS. 3*c*, 3*d*. This wedge sleeve has, at its distal end, two axially parallel projections 3.1, which are located diagonally opposite each other and between which recesses 3*a*.2 are formed. Such a wedge sleeve may also be made, in principle, flexible corresponding to the sleeve 3.1, 3.2 in its distal end area, proximally to the projections 3*a*.1, and the flexibility may likewise be brought about by slots. A wedge sleeve is preferably used for inserting a P cage.

Figure 4C:
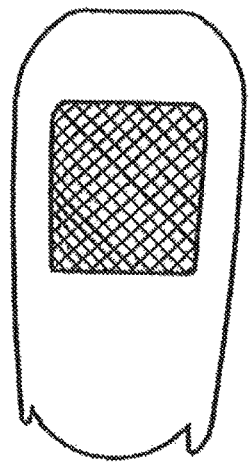
FIG. 4c is a schematic side view of a cage designed as a P-cage.
Figure 4D:
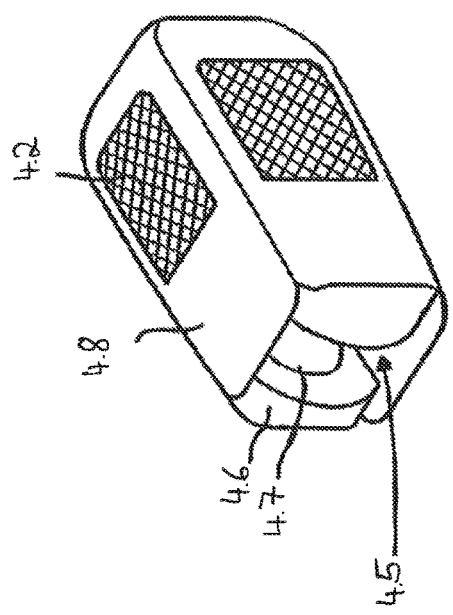
FIG. 4d is a perspective view of a P-cage.
Figure 4A:
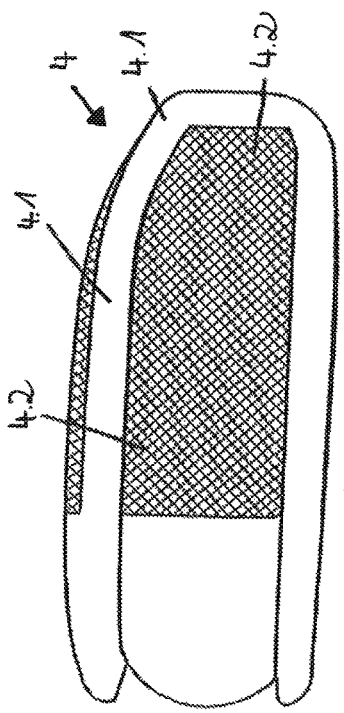
FIG. 4a is a schematic side view of a cage in the form of an O-cage.
Figure 4B:
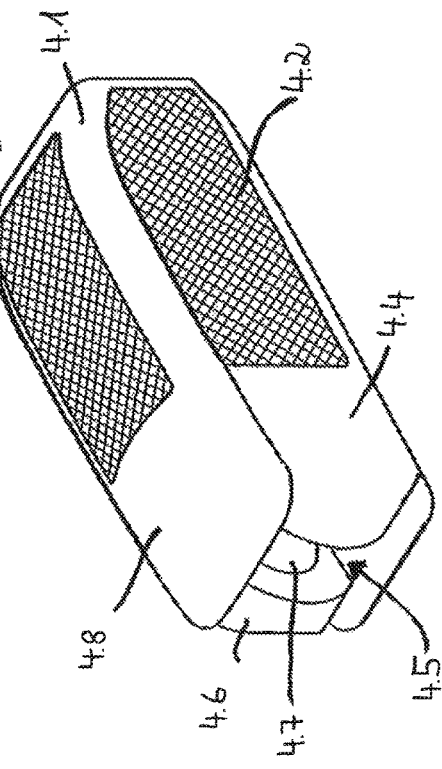

The instrument set according to the present invention includes, furthermore, at least one cage 4, designed either as an O cage or oblique cage (FIG. 4*a*, 4*b*) or as a P or posterior cage (FIG. 4*c*, 4*d*; the qualification of the cages designates the direction of insertion or the site of attachment to the patient's body), which shall be inserted into the intervertebral disk space 1.9, as well as an inserting instrument 5 (especially FIGS. 5*a*, 5*b*), by means of which the cage 4 is inserted into the intervertebral disk space 1.9 through the working sleeve 3.1 and 3.2, respectively.

The cage 4 is manufactured by electron beam melting from a titanium alloy, especially Ti6Al4V, according to ISO 5832-3, the component being manufactured by melting metal powder by means of an electron beam under high vacuum. Undercuts can be prepared hereby without lost molds or cores.

A cage 4 may have structurally three different areas: First, a massive part 4.1 as a support structure, then a core with a coarse honeycomb or lattice structure in the interior of that structure, and likewise a honeycomb or lattice structure 4.2 on the outer area of the four longitudinal sides. The lattice structure of the parts is used to make possible the integration of bone material into the cage 4 in order to make possible in this way a rigid connection between the cage and the adjacent vertebral bodies 1.1, 1.2.

The cages 4 have a length of 22 mm to 35 mm; designed as O cages, they preferably have an overall length of 34 mm and a width on the order of magnitude between 10 mm and 15 mm and different heights each between 6 mm to 16 mm, preferably equaling 8 mm, 10 mm, 12 mm or 14 mm, depending on the patient's constitution and the site of insertion or the vertebral bodies and the intervertebral disk space thereof, into which the cage shall be inserted.

With these widths and heights, the cages with the greatest height can be inserted through the working sleeve 3.2 and the other cages through the working sleeve 3.1 into the intervertebral disk space 1.9 between the vertebral bodies 1.1 and 1.2. The openings of the outer honeycomb or lattice structure may be identical and on the order of magnitude of 0.5 mm to 3.2 mm. As an alternative, there may be a coarser structure with openings of 1.5 mm to 3.2 mm in the interior and a better structure with openings of 0.5 mm to 0.7 mm on the outside.

Figure 1C:
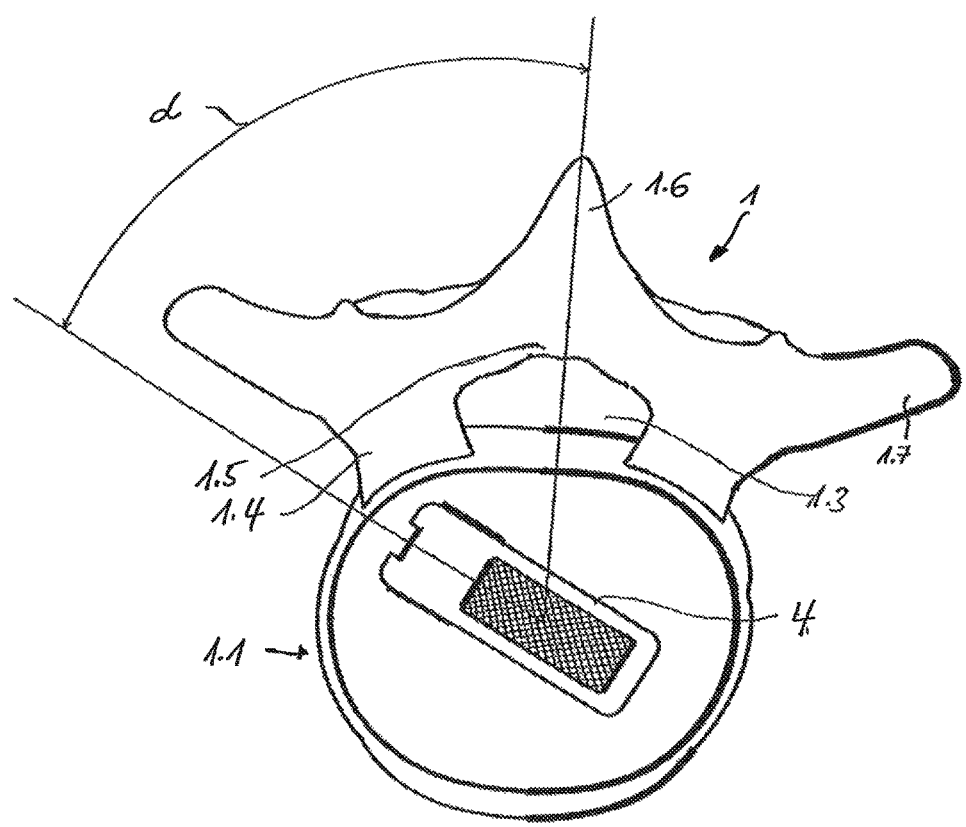
FIG. 1c is a top view of a vertebra with the cage inserted.

An O-cage (FIGS. 4*a*, 4*b*) has a length greater than 30 mm, preferably about 35 mm, and is inserted into the intervertebral disk space (specifically farther down) at an angle of about 60° in relation to the processus spinosus (FIG. 1*c*). P-cages are shorter and have, depending on the patient, a length of 24 mm to 30 mm. They are inserted into the intervertebral disk space dorsally next to the processus spinosus obliquely in relation hereto.

The inserting instrument 5 has first a grip 5.1 and a (first) outer tube 5.2, which is rigidly connected to the grip 5.1 via an intermediate part 5.1.1. A rod or—here—a (second) inner tube 5.3 extends through the outer tube 5.2.

The grip 5 has an axial perforation 5*a*, which is flush with the cavity 5.3*a* of the inner tube 5.3. The inner cavity 5.3*a* opens in a distal opening 5.3*b*. A through passage 4.4 is thus formed from the proximal end of the perforation 5.1*a* to the distal end of the inner tube 5.3 (FIG. 5*f*).

A cage 4, which likewise has a through passage, can be inserted hereby into the intervertebral space (the intervertebral disk space) via an inserted guide wire, guided by said guide wire, with the inserting instrument 5.

A locking wheel 5.3.2 is connected to the proximal end of the inner tube 5.3 via a locking clamp 5.3.1. The locking clamp 5.3.1 is rigidly connected to the inner tube 5.3 on the circumference of said inner tube 5.3. The locking clamp 5.3.1 extends through a radial perforation 5.1.2 of the intermediate part 5.1.1, which permits the rod 5.3 to be pivoted over 90° relative to the intermediate part 5.1.1 and hence also relative to the grip 5.1 and the tube 5.2. The perforation extends in an angular direction over approx. 90° for this.

At an angular position, namely, in the locked position of the distal locking element with cross bracket 5.3.3 (FIG. 5*c*), the perforation 5.1.2 extends in the proximal direction with parallel axis, so that the inner tube 5.3 is pivotable in these positions in the proximal direction together with the locking wheel 5.3.2 relative to the grip 5.1 and to the tube 5.2. Furthermore, a locking wheel 5.4 is arranged directly distally from the locking wheel 5.3.2 on the intermediate part 5.2.1, which is connected to the intermediate part 5.1.2 via a threaded connection 5.4.1.

The proximal locking parts are shown in more detail in FIG. 5*d*. Their arrangement at the inserting element can be seen in conjunction with FIGS. 5*b* and 5*c*.

FIG. 5*d* shows an enlarged view of an intermediate part 5.1.1 connected to the grip 5.1 and in this intermediate part 5.1.1 the—end-side—radial perforation 5.1.2 with the angularly extending section 5.1.2.1 thereof and an axially extending section 5.1.2.2. Laterally, there are two diagonally opposite flattened areas 5.3.5 at the proximal end of the inner tube 5.3. The locking clamp acts on these flattened areas with two pins 5.3.1.1 extending in parallel radially through the perforation 5.1.2 in an axially rigid and nonrotatable manner. The pins may move angularly into the section 5.1.2.1 and axially into the section 5.1.2.2 of the perforation.

The angular motion takes place in the released position of the locking wheel 5.4 by the locking wheel 5.3.2 acting laterally (FIGS. 5b, 5c), while the axial motion of the locking clamp is brought about by the locking wheel 5.4 itself (FIG. 5c), as was described above.

At its distal end, the inner tube 5.3 is provided with a hammer-like locking element, which has a transversely extending, distal cross bracket 5.3.3 with different height and width, always at right angles to the extension of the inner tube 5.3. The cross bracket 5.3.3 has radial projections 5.3.4 projecting radially over the inner tube 5.3 for this. An abutment 5.2.1 with parallel concave (vertical) front edges 5.2.2 is arranged at the distal end of the outer tube 5.2.

A cage 4 has on an end face an undercut opening 4.5, whose opening cross section corresponds to that of the cross bracket 5.3.3 of the inserting instrument. The undercut is formed by circular depressions 4.7 being formed on the inner sides in the proximal area of the side walls 4.6. These depressions are meshed with by the transverse projections 5.3.4 in the locked position of the locking instrument 5 with the cage 4. The undercut opening 4.5 forms a locking element at the cage 4, whereby locking of the inserting element 5 and cage 4 is made possible.

To connect the inserting instrument 5 to a cage 4, the locking wheel 5.4 is rotated on the intermediate part 5.1, via the threaded connection 5.4.1 in the distal direction (with a usual thread and clockwise view from the grip 5.1). The locking wheel 5.3.2 is released hereby and with it, the locking clamp 5.3.1, so that the latter can reach the angular area of the perforation 5.1.2 from one of the axially parallel end areas thereof.

The cross bracket 5.3.3 of the inserting instrument 5 can be inserted hereby in vertical orientation (FIGS. 5a, 5b) into the opening 4.1 of the cage 4, and the directions of the greatest extensions of the cross bracket 5.3.3 and the opening 4.5 agree. After insertion of the transverse bracket 5.3.3 through the opening 4.5 of the cage, the cross bracket 5.3.3 is pivoted by 90°. The locking wheel 5.3.2 is pivoted for this via the locking clamp 5.3.1 and with this, the rod 5.3 and the plate 5.3.3, by 90° relative to the grip 5.1 into a locked position of the cross bracket 5.3.3, so that this will mesh with the depressions 4.5 and thus extends behind the undercuts behind the opening 4.5 (FIG. 5a). The locking wheel 5.4 is subsequently screwed (counterclockwise) via the screw connection 5.4.1 relative to the grip 5.1. The locking clamp 5.3.1 is pressed hereby proximally into one of the axially parallel areas of the perforation 5.2.1 and the cross bracket 5.3.3 is thus pulled against the proximal front wall area of the cage 4, which area forms the undercut, and this cage is pulled against the abutment 5.2.1 of the inserting instrument 5 and thus braced. The strength of the bracing may be selected as desired. Especially due to the concave design of the end faces of the abutment 5.2.1, a relative pivoting of the cage 4 and insertion part 5 by up to about 15° may take place, as this is shown in FIG. 5d. Due to the insertion opening 4.5 extending up into the area of the upper wall 4.8 of the cage 4, the pivoting angle can be increased even further, preferably up to about 35° (FIG. 5e). The inserting element 5 and the cage 4 are released in a corresponding manner; the aforementioned steps are carried out essentially in the reverse order. The inserting instrument 5 and a selected cage 4 are connected to one another in the manner described above in reference to FIGS. 5a through 5d. The cage 4 is then inserted, connected to the inserting instrument 5, through the working sleeve 3.1, 3.2 into the intervertebral disk space 1.9, preferably under X-ray monitoring.

A cage 4 is inserted into the intervertebral disk space 1.9 according to the following method:

The patient is preferably in a stable lateral position (abdominal position is also possible) and is continuously responsive during the surgery under analgosedation (consequently, he does not require full anesthesia). The surgeon makes an incision in the skin of the back laterally from the spine, approximately 8-18 cm next to the processus spinosus, through which a hollow needle 2.0 is then placed first by the surgeon into the intervertebral disk space 1.9 at an angle of between 55° and 65° and preferably about 60° directly along the side of a processus spinosus facing away from the back (FIG. 6a). The spinal canal 1.3, through which the nerves pass, is not touched in the process.

Figure 6F:
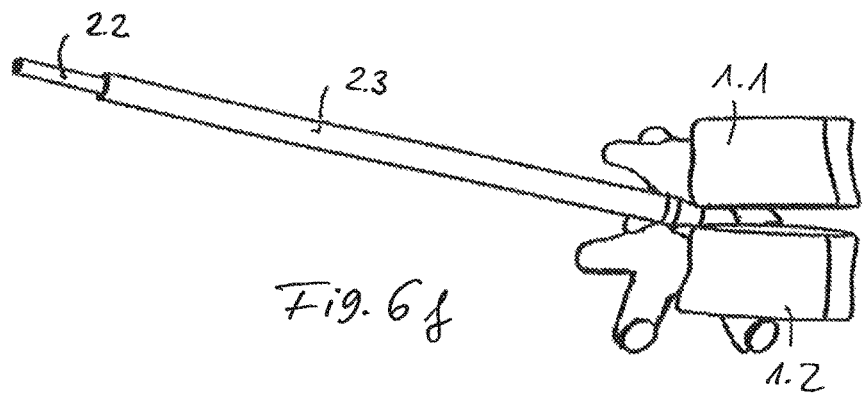
FIG. 6*f* is a view of a second dilator (guide sleeve) pushed over the first dilator of FIG. 6*e*.

A guide wire 2.1 is inserted through this needle 2.0 (FIG. 6b). The needle 2.0 is removed and the guide wire remains in place (FIG. 6c). A double-cannulated guide rod 2.2a with two eccentric holes is inserted via the guide wire 2.1 (FIG. 6d). Another wire 2.1a with greater rigidity and optionally larger diameter may be inserted by means of this guide rod 2.2a. The guide rod 2.2a and the first guide wire 2.1a remain in place. The first dilator 2.2 is subsequently pushed through the intervertebral foramen up to the intervertebral disk space 1.9 via the (second) guide wire 2.1a. The—optionally second—guide wire 2.1 and 2.1a, respectively, is then removed, and the first dilator 2.2 is used as a guide sleeve for the additional dilators 2.3 through 2.5 (or 2.6). The additional dilators 2.3, 2.4, 2.5 and possibly 2.6 are subsequently pushed consecutively over the respective, previously inserted dilator (FIGS. 6e through 6f).

Figure 6G:
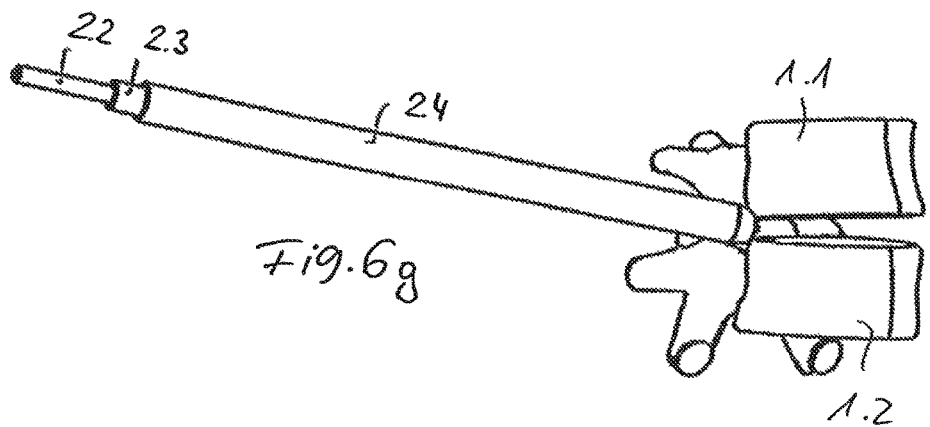
FIG. 6*g* is a view of a third dilator (guide sleeve) pushed over the first dilator of FIG. 6*e* and the second dilator of FIG. 6*f*.
Figure 6H:
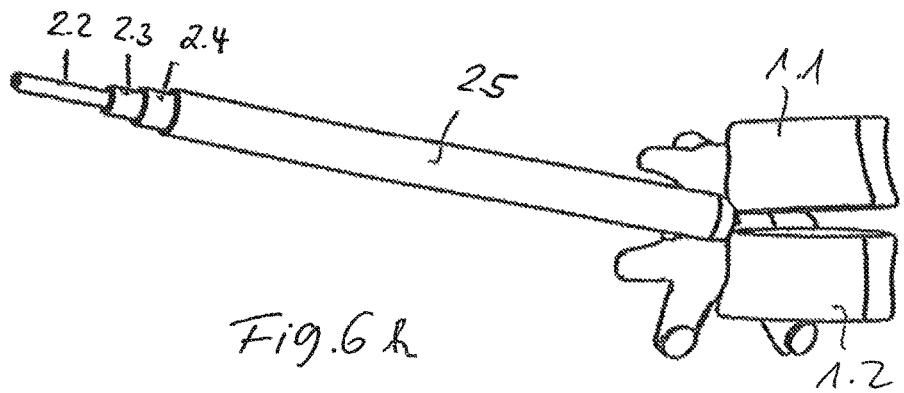
FIG. 6*h* is a view of a fourth dilator (guide sleeve) pushed over the first dilator of FIG. 6*e*, the second dilator of FIG. 6*f* and the third dilator of FIG. 6*g*.
Figure 6I:
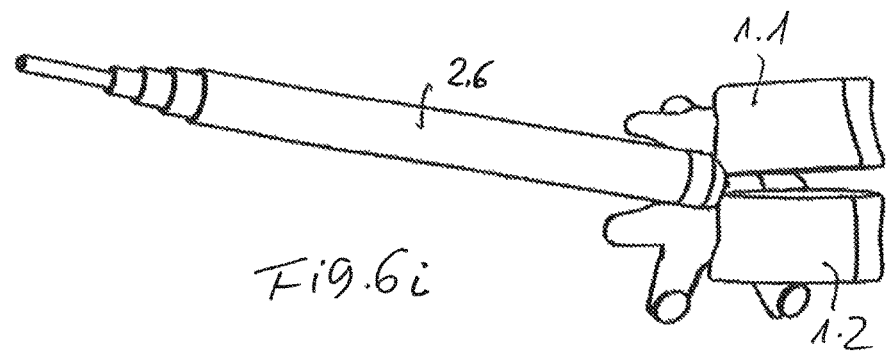
FIG. 6*i* is a view of a fifth dilator (guide sleeve) pushed over the first dilator of FIG. 6*e*, the second dilator of FIG. 6*f*, the third dilator of FIG. 6*g* and the fourth dilator of FIG. 6*h*.
Figure 6J:
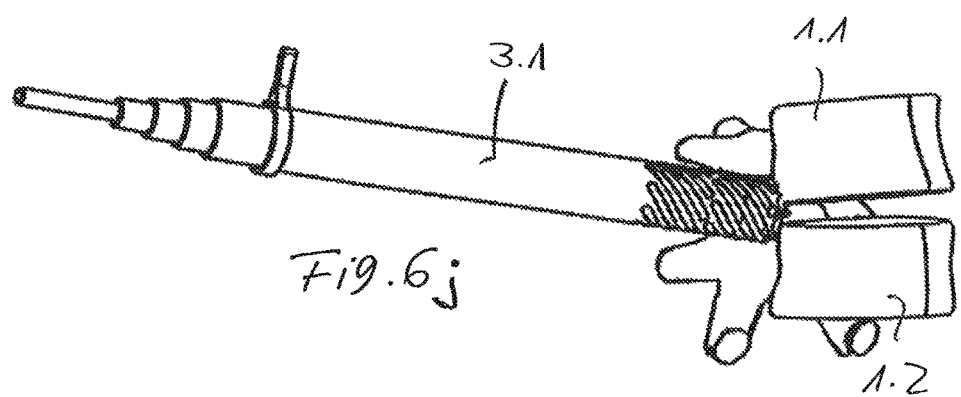
FIG. 6*j* is a working sleeve pushed over the first dilator of FIG. 6*e*, the second dilator of FIG. 6*f*, the third dilator of FIG. 6*g*, the fourth dilator of FIG. 6*h* and the fifth dilator of FIG. 6*i*.
Figure 6K:
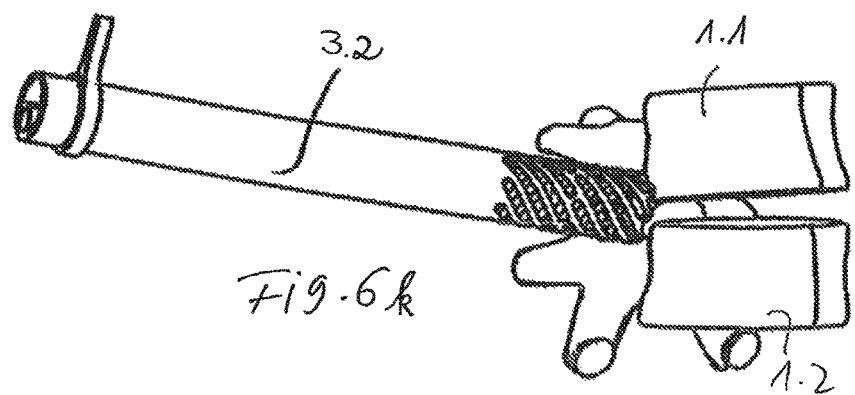
FIG. 6*k* is a view of a working sleeve of the first embodiment with a flexible distal end area, anchored on the vertebral bodies of the end face, after removal of the guide rod and the dilators.

One of the working sleeves 3, 3.2 is subsequently pushed in via the last dilator (either 2.5 or 2.6) up to the outer side of the vertebral bodies 1.1, 1.2 and anchored there with the distal, wave-shaped end face 3.6 (FIG. 6g). The dilators 2.2-2.5 (or also 2.6) are then pulled out of the working sleeve 3 and 3.2, respectively, in the proximal direction, so that only the working sleeve remains in place (FIG. 6h). A working sleeve 3a according to the second embodiment (wedge sleeve), whose end position is shown in FIG. 6i, may, in principle, also be inserted in the same manner via the dilators 2.2 through 2.5 (2.6). The projections 3a.1 mesh here with the intervertebral disk space between the adjacent vertebrae and keep the vertebrae at a distance from each other.

An endoscope 6 can now be inserted through the working sleeve (FIG. 7a) and suitable tools, such as first a mill 7, can be inserted through this under endoscopic view. Intervertebral disk material and bone tissue on the circumference of the vertebral bodies 1.1, 1.2 can be removed by means of the mill through the working sleeve 3. The intervertebral disk space 1.9 is placed with correct fit for the cages 4 (O-cage or P-cage) with mills, drills, raspatories, forceps or by shaver blades.

The mill 7 is subsequently removed from the endoscope 6 and additional instruments, especially forceps 8, 9, can be inserted through this in order to remove material of the intervertebral disk from the intervertebral disk space 1.9 (FIG. 7b).

The vertebral bodies can be kept at a distance from each other in a suitable manner, such as by pedicle screws, wedge sleeves or the like (which is not the subject of the present invention).

Figure 8B:
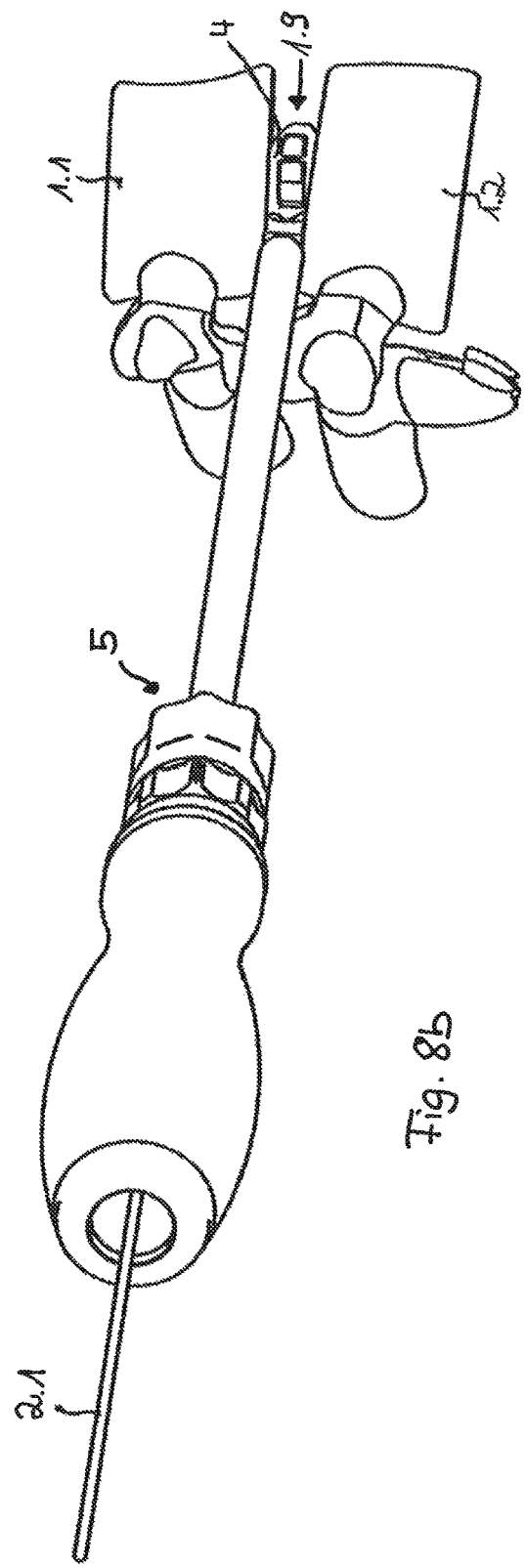
FIG. 8*b* is another view showing the course of insertion of the cage by means of the insertion tool via the guide wire into the intervertebral space.
Figure 8C:
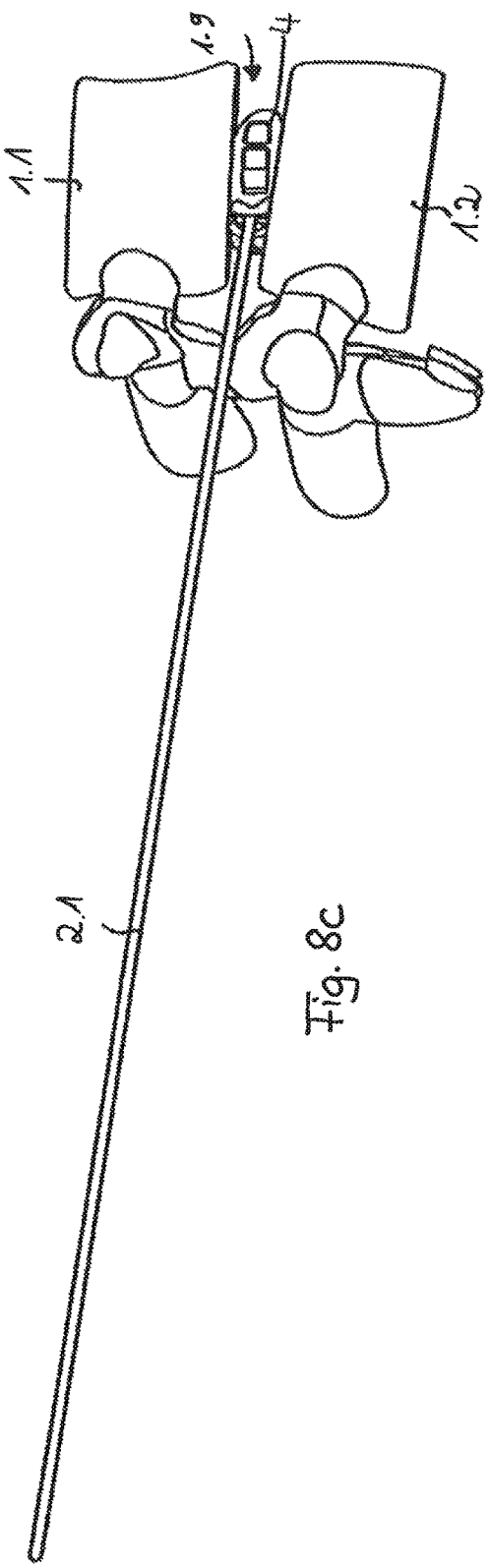
FIG. 8*c* is yet another view showing the course of insertion of the cage by means of the insertion tool via the guide wire into the intervertebral space.

After removal of the intervertebral disk material from the intervertebral disk space 1.9, the endoscope 6 and the tools 8, 9 are removed from the working sleeve 3. The cage 4 is subsequently inserted into the instrument set through the working sleeve 3 by means of the inserting instrument 5, as this is shown in FIGS. 8a-8c. The cage 4 is inserted into the intervertebral disk space 1.9 under X-ray monitoring, and the material of the cage 4 (titanium alloy with a honeycomb structure) makes good observation of the insertion possible.

The working sleeve, which continued to be connected corresponding to FIG. 6h or 6d, was not shown in FIGS. 8a-8c in the views showing the insertion of a cage 4 into the intervertebral disk space 1.9 for the sake of greater clarity.

If the guide wire 2.1 or 2.1a was removed and is not left in place during the removal of the intervertebral disk by means of tools operating through the endoscope 6 (FIG. 7a, b), a guide wire 2.1 or 2.1a is inserted again through the endoscope 6 before the removal thereof and the endoscope is then removed. According to FIG. 8a, a guide wire, for example, a guide wire 2.1, and the working sleeve (not shown for the aforementioned reasons) will then be located in the body of the patient. A cage 4 connected to an insertion tool 5 in the above-described manner is then pushed into the intervertebral disk space 1.9 by means of the inserting instrument 5 via the guide wire 2.1 and through the working sleeve (FIG. 8b).

After insertion of the cage 4 by means of the inserting instrument 5 into the intervertebral disk space 1.9 and suitable positioning in this, the locking is released by means of the locking wheel 5.4 and the plate 5.3.3 is rotated back by means of the locking wheel 5.3.2 (FIGS. 5b, 5c), as a result of which the inserting element 5 can be separated from the cage 4 and the inserting element 5 can be removed from the working sleeve 3 or the guide wire 2.1 through the working sleeve 3.

The cage 4 is subsequently also checked and inspected directly in respect to its position with the endoscope 6. The cage 4 may also be filled additionally with bone (bone replacement material) through the visible depression (undercut) under endoscopic monitoring. Finally, the guide wire 2.1 and the working sleeve 3 are also removed, while the cage 4 remains in the intervertebral disk space 1.9. The working sleeve 3 is subsequently removed, the wound is closed and treated, and the surgery is thus completed.

The two vertebrae defining the intervertebral disk space are also braced within the framework of the surgical procedure by means of a screw-and-rod system, pedicle screws or the like. This is not the subject of the present invention and is not therefore shown and described.

While specific embodiments of the invention have been shown and described in detail to illustrate the application of the principles of the invention, it will be understood that the invention may be embodied otherwise without departing from such principles.

The invention claimed is:

1. An instrument set for inserting a cage into an intervertebral disk space between two vertebral bodies, the instrument set comprising:
   a guide wire;
   a plurality of dilators that can be pushed over the guide wire and one over another;
   a working sleeve; and
   a cage, the working sleeve comprising slots with ribs located between said slots extending helically over one half of a circumference around a distal area of the working sleeve, the ribs being connected by webs separating aligned slots providing a flexible distal jacket area, said flexible distal jacket area comprising one fourth to one third of a length of the working sleeve.

2. An instrument set in accordance with claim 1, wherein each of the webs is arranged between one of the slots and another one of the slots.

3. An instrument set in accordance with claim 1, wherein widths of the slots, the ribs and webs are between 0.5 mm and 2 mm.

4. An instrument set in accordance with claim 1, wherein the working sleeve is a wedge sleeve such that said wedge sleeve has diagonally opposite projections extending axially in parallel in a distal end area of said wedge sleeve, leaving recesses free.

5. An instrument set in accordance with claim 4, wherein the projections are provided with a rounding each at a distal free end.

6. An instrument set in accordance with claim 1, wherein the cage and an inserting instrument for inserting the cage have locking elements, which interact each with one another, and which form a common locking.

7. An instrument set in accordance with claim 6, wherein locking of the inserting instrument and the cage permits an angular mobility of the inserting instrument and the cage.

8. An instrument set in accordance with claim 1, wherein the cage has an opening with a height that is greater than a width as a locking element on an end face, wherein the opening is provided with an undercut in a direction of a width of the opening.

9. An instrument set in accordance with claim 1, wherein an inserting element has a rod or an inner tube with a radially extending plate, which comprises a locking element at the distal end, extends radially and said radially extending plate has a greater width than a height, and said radially extending plate is pivotable about an axis of the rod by means of a grip.

10. An instrument set in accordance with claim 9, wherein the inserting instrument has an outer tube, through which the rod extends, so that the plate is pivotable relative to the tube and by which the grip sleeve can be locked.

11. An instrument set in accordance with claim 10, wherein an abutment at the outer tube with two convex front edges extending in parallel to one another.

12. An instrument set in accordance with claim 6, wherein each of the inserting instrument and the cage has a through passage.

13. An instrument in accordance with claim 1, wherein the cage is provided with grid areas or lattice areas.

14. An instrument in accordance with claim 13, wherein one or more:
   the grid areas have opening diameters of each opening ranging from 0.5 mm to 3.2 mm, and each opening has opening diameters on an order of magnitude of 0.5 mm to 0.7 mm on an outer side of the cage;
   lattice areas in an interior of the cage have openings or perforations with diameters of 1.5 mm to 3.2 mm.

15. A method for inserting a cage into an intervertebral disk space between two vertebral bodies, the method comprising:
   inserting a hollow needle;
   inserting a guide wire through said hollow needle into the intervertebral disk space;
   removing the hollow needle;
   pushing dilators with consecutively larger diameters over the guide wire one after another and one over another after removing the hollow needle;
   inserting a working sleeve over a last one of the dilators up to the vertebral bodies, wherein the guide wire and the dilators are removed from the working sleeve, said working sleeve comprising slots with ribs located between said slots extending helically over one half of a circumference around a distal area of the working sleeve, the ribs being connected by webs separating aligned slots providing a flexible distal jacket area, said flexible distal jacket area comprising one fourth to one third of a length of the working sleeve;

pushing a cage with an at least partially porous structure into the intervertebral disk space through the working sleeve via an inserting instrument, with which the cage is locked, wherein a locking between the cage and the inserting instrument is released after removal of an intervertebral disk from the intervertebral disk space, and the working sleeve is removed, said working sleeve comprising slots in a distal jacket area thereof and ribs arranged between said slots, the ribs being connected by webs separating aligned slots.

16. A method for inserting a cage into an intervertebral disk space between two vertebral bodies, the method comprising:

inserting a hollow needle and then inserting a guide wire through said hollow needle up into the intervertebral disk space, wherein the hollow needle is removed, and dilators with consecutively larger diameters are then pushed over the guide wire one after another and one over another, wherein a working sleeve is then inserted via a last one of the dilators up to the two vertebral bodies, and the guide wire and the dilators are removed from the working sleeve, the working sleeve comprising slots with ribs located between said slots extending helically over one half of a circumference around a distal area of the working sleeve, the ribs being connected by webs separating aligned slots providing a flexible distal jacket area, said flexible distal jacket area comprising one fourth to one third of a length of the working sleeve;

inserting instruments transcutaneously from a back of the working sleeve at an angle greater than 50° and less than 70° in relation to a processus spinosus up to the vertebral body, said working sleeve comprising slots in a distal jacket area thereof and ribs arranged between said slots, the ribs being connected by webs, the webs separating aligned slots.

17. A method in accordance with claim 16, wherein the instruments are inserted to the vertebral bodies from the back on a side of a transverse process facing away from dorsal surfaces and after removal of an intervertebral disk from the intervertebral disk space through the working sleeve, a cage with an at least partially porous structure is pushed into the intervertebral disk space by means of at least one of the inserting instruments, after which locking between the cage and the at least one of the inserting instruments and the working sleeve are then removed, wherein two adjacent ribs are connected via the webs.

18. A method in accordance with claim 15, wherein said working sleeve being inserted by a screwing motion via the dilators, each of the webs being arranged between one of the slots another one of the slots, the distal jacket area defining an outer surface of the working sleeve, said working sleeve having a sleeve wall, said sleeve wall having an outer side and an inner side, each of said slots extending from said inner side to said outer side in a radial direction with respect to a longitudinal axis of said working sleeve.

19. A method in accordance with claim 16, wherein a cage having a porous design is inserted into the intervertebral disk space through the working sleeve, each of the webs being arranged between one of the slots another one of the slots, wherein each of the slots has a radial extent equal to a thickness of the working sleeve with respect to a longitudinal axis of the working sleeve.

20. A method in accordance with claim 19, wherein said cage comprises a porosity that is greater on an inside thereof and finer on an outer area thereof.

21. An instrument set in accordance with claim 1, wherein each of said slots extends along only a portion of a circumferential surface of said distal jacket, said working sleeve having a sleeve wall, said sleeve wall having an outer side and an inner side, each of said slots extending from said inner side to said outer side in a radial direction with respect to a longitudinal axis of said working sleeve.

22. An instrument set in accordance with claim 1, wherein each of said slots is defined by only a portion of a circumferential surface of said distal jacket, said working sleeve having a sleeve wall, said sleeve wall having a sleeve wall thickness, each of said slots having a radial extent equal to said sleeve wall thickness.

23. A method in accordance with claim 16, wherein said distal jacket area is integrally connected to the working sleeve to define a one-piece working sleeve structure, each of said slots extending from an inner side of said working sleeve to an outer side of said working sleeve in a radial direction with respect to a longitudinal axis of said working sleeve.

24. An instrument set in accordance with claim 1, wherein said working sleeve has a sleeve wall, said sleeve wall having an outer surface and an inner surface, each slot having a first end and a second end, said first end being located directly adjacent to said outer surface, said second end being located directly adjacent to said inner surface.

* * * * *